(12) United States Patent
Yun et al.

(10) Patent No.: US 11,311,777 B2
(45) Date of Patent: Apr. 26, 2022

(54) ELECTRONIC DEVICE FOR PROVIDING EXERCISE INFORMATION USING BIOMETRIC INFORMATION AND OPERATING METHOD THEREOF

(71) Applicant: Samsung Electronics Co., Ltd., Suwon-si (KR)

(72) Inventors: Inho Yun, Suwon-si (KR); Jinho Kim, Suwon-si (KR); Seunghwan Shin, Suwon-si (KR); Junseok Oh, Suwon-si (KR); Sunghwan Cho, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 62 days.

(21) Appl. No.: 16/431,024

(22) Filed: Jun. 4, 2019

(65) Prior Publication Data

US 2019/0374816 A1  Dec. 12, 2019

(30) Foreign Application Priority Data

Jun. 7, 2018  (KR) .................. 10-2018-0065372

(51) Int. Cl.
*A63B 24/00* (2006.01)
*A61B 5/00* (2006.01)
(Continued)

(52) U.S. Cl.
CPC ........ *A63B 24/0075* (2013.01); *A61B 5/0002* (2013.01); *A61B 5/0205* (2013.01);
(Continued)

(58) Field of Classification Search
CPC .......... A61B 5/0205; A61B 2562/0219; A61B 5/681; A63B 24/0075
See application file for complete search history.

(56) References Cited

U.S. PATENT DOCUMENTS 9,704,412 B2  7/2017 Wells et al.
2007/0249467 A1  10/2007 Hong et al.
(Continued)

FOREIGN PATENT DOCUMENTS

EP  3 153 093 A1  4/2017

OTHER PUBLICATIONS

International Search Report and Written Opinion dated Sep. 17, 2019, issued in International Patent Application No. PCT/KR2019/006736.

(Continued)

*Primary Examiner* — Carl H Layno
*Assistant Examiner* — Aya Ziad Bakkar
(74) *Attorney, Agent, or Firm* — Jefferson IP Law, LLP

(57) ABSTRACT

An electronic device is provided. The electronic device includes a housing, a touch screen display to be exposed through a first portion of the housing, a motion sensor disposed inside the housing, a photoplethysmography (PPG) sensor disposed in a second portion of the housing, a processor operatively coupled to the display, the motion sensor, and the PPG sensor, and a memory operably coupled to the processor. The memory stores instructions that allow, when executed, the processor to receive first data from the motion sensor, identify whether a user has started exercise based on at least a portion of the first data, receive second data from the PPG sensor after identifying whether or not the user has started exercise, and determine the type of exercise of the user based on at least a portion of the first data and the second data.

19 Claims, 31 Drawing Sheets

(51) Int. Cl.
    *A61B 5/0205* (2006.01)
    *A61B 5/021* (2006.01)
    *A61B 5/024* (2006.01)
    *A61B 5/11* (2006.01)

(52) U.S. Cl.
    CPC .............. *A61B 5/486* (2013.01); *A61B 5/681* (2013.01); *A61B 5/6898* (2013.01); *A61B 5/742* (2013.01); *A61B 5/021* (2013.01); *A61B 5/02416* (2013.01); *A61B 5/02438* (2013.01); *A61B 5/1123* (2013.01); *A61B 2562/0219* (2013.01); *A61B 2562/0257* (2013.01); *A63B 2024/0071* (2013.01)

(56) References Cited

U.S. PATENT DOCUMENTS

| | | | |
|---|---|---|---|
| 2013/0253943 A1* | 9/2013 | Lee et al. | G16H 50/20 705/2 |
| 2014/0197963 A1 | 7/2014 | Park et al. | |
| 2015/0112154 A1 | 4/2015 | He et al. | |
| 2015/0112156 A1 | 4/2015 | He et al. | |
| 2015/0112157 A1 | 4/2015 | Bijjani et al. | |
| 2016/0367172 A1 | 12/2016 | Kuroda et al. | |
| 2017/0209055 A1* | 7/2017 | Pantelopoulos | A61B 5/720=3 |
| 2018/0055375 A1* | 3/2018 | Martinez | A61B 5/318 |
| 2018/0078192 A1* | 3/2018 | Chen | A61B 5/1116 |

OTHER PUBLICATIONS

Extended European Search Report dated Aug. 13, 2019, issued in European Patent Application No. 19178462.8.
European Office Action dated Apr. 9, 2020, issued in European Application No. 19178462.8.
European Office Action dated Nov. 19, 2020, issued in European Application No. 19178462.8.
Tapia, E. et al., "Real-time recognition of physical activities and their intensities using wireless accelerometers and a heart monitor" in Proc. International Symposium on Wearable Computers, 2007, pp. 37-40. [retrieved from internet Feb. 1, 2022].
Cornacchia, M. et al., "A Survey on Activity Detection and Classification Using Wearable Sensors", IEEE Sensors Journal, vol. 17, No. 2, pp. 386-403, Jan. 15, 2017, doi: 10.1109/JSEN.2016.2628346. [retrieved from internet Feb. 1, 2022].
Morris, D., "RecoFit: Using a Wearable Sensor to Find, Recognize, and Count Repetitive Exercises", Session: Applications of Body Sensing, CHI 2014, One of a CHInd, Toronto, ON, Canada, DOI:10.1145/2556288.2557116 [retrieved from internet Feb. 2, 2022].
Australian Office Action dated Feb. 3, 2022, issued in Australia Patent Application No. 2019283484.

* cited by examiner

ELECTRONIC DEVICE FOR PROVIDING EXERCISE INFORMATION USING BIOMETRIC INFORMATION AND OPERATING METHOD THEREOF

CROSS-REFERENCE TO RELATED APPLICATION(S)

This application is based on and claims priority under 35 U.S.C. § 119(a) of a Korean patent application number 10-2018-0065372, filed on Jun. 7, 2018, in the Korean Intellectual Property Office, the disclosure of which is incorporated by reference herein in its entirety.

BACKGROUND

1. Field

The disclosure relates to an electronic device for providing analysis information of exercise performed by a user and exercise guidance information conforming to the characteristics of a user using changes in the biometric information of a user, and an operating method thereof.

2. Description of Related Art

Portable electronic devices, such as smart phones, provide more complex services, such as games, instant messaging, document editing, image/video playback and editing, and the like, as well as basic services such as phone calls and text messaging.

As modern people's interest in health is growing, modern people have come to perform various kinds of exercise according to different exercise purposes. For example, those who wish to increase muscular strength or muscle mass may primarily focus on strength training (or static exercise), such as squats or lateral raises, and those who wish to lose fat and weight may concentrate on aerobic exercise such as running or cycling.

In addition, since a wearable device, which is worn on a user's body such as a wrist, is usually in contact with or close to the user's body for a long time, the wearable device may be utilized to obtain various and accurate biometric information of the user who performs exercise.

The wearable device or a portable electronic device connected to the wearable device may provide the user with information on the exercise performed by the user using the obtained biometric information of the user. For example, a smart phone may obtain information on the exercise time of the user and the number of calories consumed by the exercise, or may provide the same to the user using acceleration sensor information and heart rate sensor information, which are obtained by the wearable device.

The above information is presented as background information only to assist with an understanding of the disclosure. No determination has been made, and no assertion is made, as to whether any of the above might be applicable as prior art with regard to the disclosure.

SUMMARY

An electronic device including a wearable device may use biometric information of a user in order to provide a user with information about the exercise performed by the user. In this case, the biometric information of the user may be data sensed by a sensor provided in the electronic device, and may be, for example, acceleration information and heart rate information sensed by an acceleration sensor and a heart rate sensor.

Since the acceleration sensor provides information only about simple motion of the user, it is not sufficient to provide information about the intensity of the exercise performed by the user. For example, if the user performs an isolated exercise (e.g., a plank) in which the whole body does not move, the exercise intensity information based on the acceleration sensor may be inaccurate. In addition, the heart rate sensor may also provide incorrect exercise intensity information depending on the type of exercise performed by the user. For example, when a user performs aerobic exercise (e.g., running) or static exercise (e.g., squat) at the same intensity, an electronic device based on the heart rate sensor may make inaccurate judgment in which the user performed the aerobic exercise with a higher exercise intensity than the static exercise. If the electronic device fails to provide the user with an accurate judgment about the exercise performed by the user as described above, the user is not able to perform the optimal exercise for his/her exercise purpose. Thus, there is increasing need to provide users with accurate exercise information including the exercise intensity for a wide variety of exercises.

Aspects of the disclosure are to address at least the above-mentioned problems and/or disadvantages and to provide at least the advantages described below. Accordingly, an aspect of the disclosure is to provide an apparatus and method for determining the type of exercise performed by a user using blood pressure data of a user, which is sensed by a photoplethysmography (PPG) sensor, as well as data sensed by existing sensors (such as an acceleration sensor or a heart rate sensor), and may provide the user with information on the intensity of the exercise performed by the user on the basis of the determined type of exercise. In addition, various embodiments of the disclosure may update information on the intensity of the exercise performed by the user, or may provide the user with guidance information on subsequent exercise to be performed by the user using feedback data received from the user.

The technical subjects sought by the disclosure are not limited to the technical subjects mentioned above, and other technical subjects which are not mentioned above may be clearly understood by those skilled in the art on the basis of the following description.

Additional aspects will be set forth in part in the description which follows and, in part, will be apparent from the description, or may be learned by practice of the presented embodiments.

In accordance with an aspect of the disclosure an electronic device is provided. The electronic device includes a housing, a display exposed through a first portion of the housing, a motion sensor disposed inside the housing, a PPG sensor disposed in a second portion of the housing, a processor operatively coupled to the display, the motion sensor, and the PPG sensor, and a memory operably coupled to the processor. The memory stores instructions that, when executed, cause the processor to receive first data from the sensors, identify whether a user has started exercise based on at least a portion of the first data, receive second data from the PPG sensor after identifying whether the user has started exercise, store the type, time, intensity, and the like of the exercise performed by the user based on at least a portion of the first data and the second data, and receive user feedback.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the disclosure will be more apparent from the following description taken in conjunction with the accompanying drawings, in which.

Throughout the drawings, it should be noted that like reference numbers are used to depict the same or similar elements, features, and structures.

DETAILED DESCRIPTION

The following description with reference to the accompanying drawings is provided to assist in a comprehensive understanding of various embodiments of the disclosure as defined by the claims and their equivalents. It includes various specific details to assist in that understanding, but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but are merely used by the inventor to enable a clear and consistent understanding of the disclosure. Accordingly, it should be apparent to those skilled in the art that the following description of various embodiments of the disclosure is provided for illustration purposes only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Figure 1:
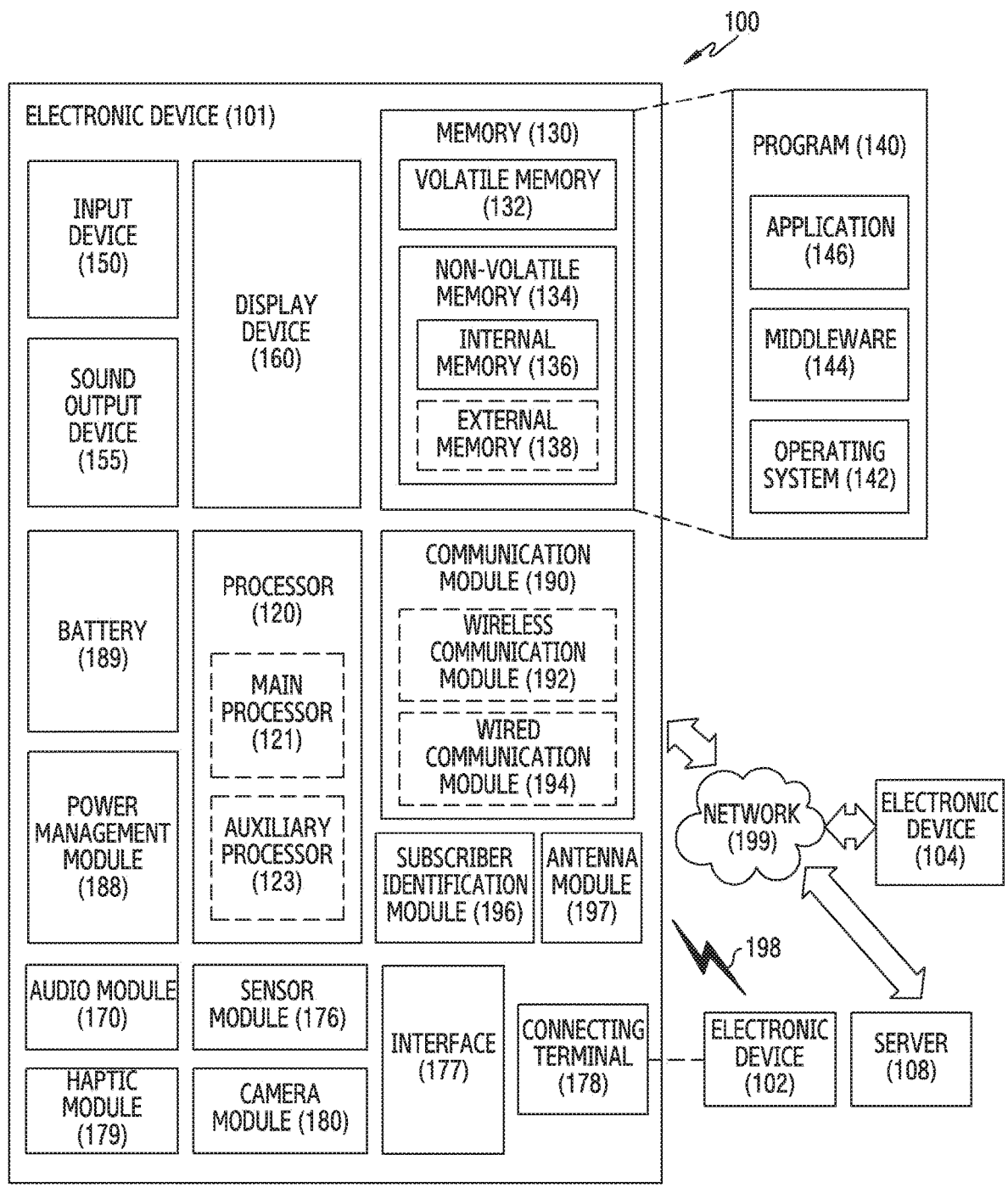
FIG. 1 is a block diagram of an electronic device in a network environment according to an embodiment of the disclosure.

FIG. 1 is a block diagram illustrating an electronic apparatus in a network environment according to an embodiment of the disclosure.

Referring to FIG. 1, in the network environment 100, the electronic apparatus 101 may communicate with an electronic apparatus 102 via a first network 198 (e.g., a short-range wireless communication network) or may communicate with an electronic apparatus 104 or a server 108 via a second network 199 (e.g., a long-range wireless communication network). The electronic apparatus 101 may communicate with the electronic apparatus 104 via the server 108. The electronic apparatus 101 may include a processor 120, a memory 130, an input device 150, a sound output device 155, a display device 160, an audio module 170, a sensor module 176, an interface 177, a connecting terminal 178, a haptic module 179, a camera module 180, a power management module 188, a battery 189, a communication module 190, a subscriber identity module 196, or an antenna module 197. In some embodiments, at least one (e.g., the display device 160 or the camera module 180) of these components may be omitted, or one or more other components may be further included in the electronic apparatus 101. In some embodiments, some of these components may be configured as an integrated circuit. For example, the sensor module 176 (e.g., a fingerprint sensor, an iris sensor, or an illumination sensor) may be embedded in the display device 160 (e.g., a display).

The processor 120 may run, for example, software (e.g., a program 140) to control at least one other component (e.g., a hardware or software component) of the electronic apparatus 101 connected to the processor 120, and may perform various types of data processing or arithmetic operations. As at least part of the data processing or operations, the processor 120 may load a command or data received from another component (e.g., the sensor module 176 or the communication module 190) into a volatile memory 132, may process the command or data stored in the volatile memory 132, and may store the resulting data in a non-volatile memory 134. According to one embodiment, the processor 120 may include a main processor 121 (e.g., a central processing unit or an application processor) and a coprocessor 123 (e.g., a graphics processing unit, an image signal processor, a sensor hub processor, or a communications processor) that is operable independently of or together with the main processor 121. Additionally or alternatively, the coprocessor 123 may be configured to use lower power than the main processor 121 or to specialize in a designated function. The coprocessor 123 may operate separately from the main processor 121 or as a part thereof.

The coprocessor 123 may control at least some of the functions or states associated with at least one component (e.g., the display device 160, the sensor module 176, or the communication module 190) among the components of the electronic apparatus 101, for example, instead of the main processor 121 when the main processor 121 is in an inactive (e.g., sleep) state, or along with the main processor 121 when the main processor 121 is in an active (e.g., application-running) state. The coprocessor 123 (e.g., an image signal processor or a communications processor) may be configured as a part of another functionally related component (e.g., the camera module 180 or the communication module 190).

The memory 130 may store various data used by at least one component (e.g., the processor 120 or the sensor module 176) of the electronic apparatus 101. The data may include, for example, software (e.g., the program 140), and input data or output data about a command associated with the software. The memory 130 may include a volatile memory 132 or a non-volatile memory 134.

The program 140 may be stored as software in the memory 130 and may include, for example, an operating system 142, middleware 144, or an application 146.

The input device 150 may receive a command or data to be used for a component (e.g., the processor 120) of the electronic apparatus 101 from the outside (e.g., a user) of the electronic apparatus 101. The input device 150 may include, for example, a microphone, a mouse, or a keyboard.

The sound output device 155 may output a sound signal to the outside of the electronic apparatus 101. The sound output device 155 may include, for example, a speaker or a receiver. The speaker may be employed for general use, such as for multimedia playback or recording playback, and the receiver may be used for receiving an incoming call. The receiver may be configured separately from the speaker or as a part of the speaker.

The display device 160 may visually provide information to the outside (e.g., a user) of the electronic apparatus 101. The display device 160 may include, for example, a display, a hologram device, or a projector and a control circuit for controlling a corresponding device. The display device 160 may include touch circuitry configured to detect a touch or sensor circuitry (e.g., a pressure sensor) configured to measure the strength of force generated by a touch.

The audio module 170 may convert a sound into an electrical signal, or, conversely, an electrical signal into a sound. The audio module 170 may acquire a sound through the input device 150 or may output a sound through the sound output device 155 or an external electronic apparatus (e.g., the electronic apparatus 102 (e.g., a speaker or a headphone)) connected directly or wirelessly to the electronic apparatus 101.

The sensor module 176 may detect an operating state (e.g., power or temperature) of the electronic apparatus 101 or an external environmental condition (e.g., a user's condition) and may generate an electrical signal or a data value corresponding to the detected state or condition. The sensor module 176 may include, for example, a gesture sensor, a gyro sensor, a barometric pressure sensor, a magnetic sensor, an acceleration sensor, a grip sensor, a proximity sensor, a color sensor, an infrared (IR) sensor, a biometric sensor, a temperature sensor, a humidity sensor, or an illumination sensor.

The interface 177 may support one or more designated protocols that can be used for the electronic apparatus 10 to be directly or wirelessly connected to an external electronic apparatus (e.g., the electronic apparatus 102). According to one embodiment, the interface 177 may include, for example, a high-definition multimedia interface (HDMI), a universal serial bus (USB) interface, a secure digital (SD) card interface, or an audio interface.

The connection terminal 178 may include a connector through which the electronic apparatus 101 can be physically connected to an external electronic apparatus (e.g., the electronic apparatus 102). The connection terminal 178 may include, for example, as an HDMI connector, a USB connector, an SD card connector, or an audio connector (e.g., a headphone connector).

The haptic module 179 may convert an electrical signal into a mechanical stimulus (e.g., vibrations or a movement) or an electrical stimulus that is perceivable by the user through a tactile sensation or the sense of movement. The haptic module 179 may include, for example, a motor, a piezoelectric element, or an electrical stimulation device.

The camera module 180 may capture a still image and a moving image. According to one embodiment, the camera module 180 may include one or more lenses, image sensors, image signal processors, or flashes.

The power management module 188 may manage the power supplied to the electronic apparatus 101. The power management module 188 may be configured, for example, as at least a part of a power management integrated circuit (PMIC).

The battery 189 may supply power to at least one component of the electronic apparatus 101. The battery 189 may include, for example, a non-rechargeable primary battery, a rechargeable secondary battery, or a fuel cell.

The communication module 190 may support establishing a direct (e.g., wired) communication channel or a wireless communication channel between the electronic apparatus 101 and an external electronic apparatus (e.g., the electronic apparatus 102, the electronic apparatus 104, or the server 108) and performing communication through the established communication channel. The communication module 190 may include one or more communication processors that operate independently of the processor 120 (e.g., an application processor) and support direct (e.g., wired) communication or wireless communication. The communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power-line communication module). Among these communication modules, a corresponding communication module may communicate with an external electronic apparatus via the first network 198 (e.g., a short-range wireless communication network including a Bluetooth, Wi-Fi direct, or IR data association (IrDA) network) or the second network 199 (e.g., a long-range wireless communication network including a cellular network, the Internet, or a computer network (e.g., a LAN or wide area network (WAN))). These various types of communication modules may be integrated into one component (e.g., a single chip) or may be configured as a plurality of separate components (e.g., a plurality of chips). The wireless communication module 192 may identify and authenticate the electronic apparatus 101 within a communication network, such as the first network 198 or the second network 199, using subscriber information (e.g., an international mobile subscriber identity (IMSI)) stored in the subscriber identity module 196.

The antenna module 197 may transmit a signal or power to the outside (e.g., an external electronic apparatus) or may receive a signal or power from the outside. The antenna module 197 may include one or more antennas, among which at least one antenna suitable for a communication mode used for a communication network, such as the first network 198 or the second network 199, may be selected, for example, by the communication module 190. A signal or power may be transmitted or received between the communication module 190 and an external electronic apparatus via the at least one selected antenna.

At least some of the components may be connected to each other via a communication mode between peripheral devices (e.g., a bus, general-purpose input and output (GPIO), serial peripheral interface (SPI), or mobile industry processor interface (MIPI)) and may exchange signals (e.g., a command or data) with each other.

According to one embodiment, a command or data may be transmitted or received between the electronic apparatus 101 and the external electronic apparatus 104 via the server 108 connected to the second network 199. Each of the electronic apparatuses 102 and 104 may be a device of the same kind or a different kind from the electronic apparatus 101. All or some operations performed by the electronic apparatus 101 may be performed by one or more external electronic apparatuses among the external electronic apparatuses 102, 104, or 108. For example, when the electronic apparatus 101 needs to perform a function or a service automatically or upon request from a user or another device, the electronic apparatus 101 may, instead of or in addition to autonomously executing the function or the service, request at least one or more external electronic apparatuses to perform at least part of the function or the service. Upon receiving such a request, the one or more external electronic apparatuses may execute the at least part of the requested function or service or an additional function or service associated with the request, and may transmit the result of execution thereof to the electronic apparatus 101. The electronic apparatus 101 may provide the result, as at least part of a response to the request, without any processing or via additional processing. To this end, for example, cloud-computing, distributed-computing, or client-server-computing technologies may be used.

Figure 2A:
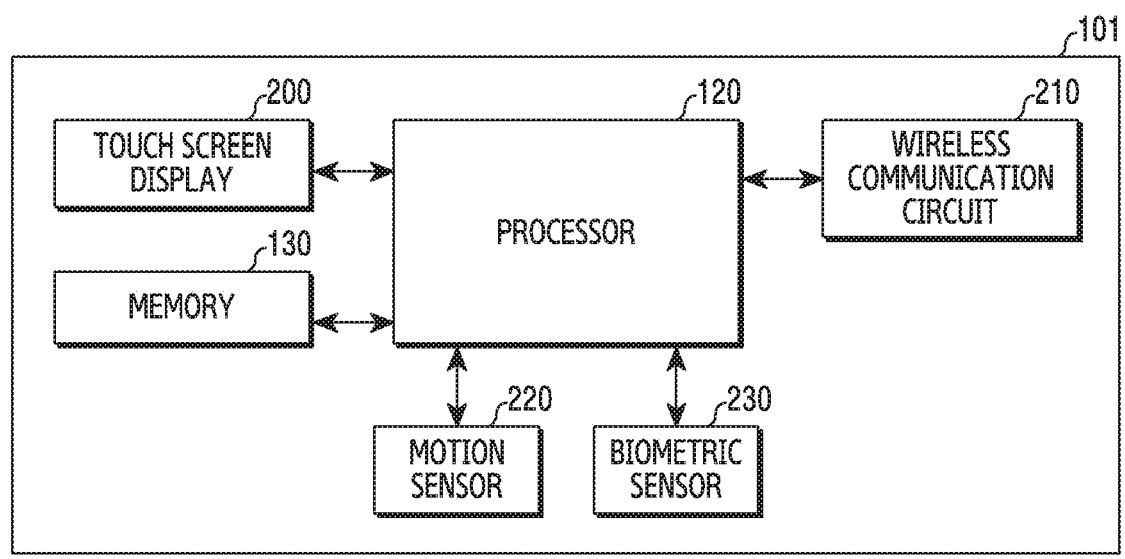
FIG. 2A is a diagram for explaining an electronic device according to an embodiment of the disclosure.

FIG. 2A is a diagram for explaining an electronic device (e.g., the electronic device 101 in FIG. 1) according to an embodiment of the disclosure.

Referring to FIG. 2A, the electronic device 101 may include the processor 120, the memory 130, a touch screen display 200, a wireless communication circuit 210, a motion sensor 220, and/or a biometric sensor 230.

The processor 120 may execute software (e.g., the programs 140 in FIG. 1) to control at least one of other elements of the electronic device 101 (e.g., the memory 130, the touch screen display 200, the wireless communication circuit 210, the motion sensor 220, and/or the biometric sensor 230) connected to the processor 120, and may perform various data processes or calculations. The processor 120 may process various signals obtained from the biometric sensor 230 (e.g., a photoplethysmography (PPG) sensor). For example, the processor 120 may process a PPG signal provided from the biometric sensor 230 (e.g., a PPG sensor). The processor 120 may process the PPG signal on the basis of a pulse wave analysis (PWA) scheme. The processor 120 may identify blood pressure information of a user (e.g., systolic blood pressure (SBP) and diastolic blood pressure (DBP)) from the PPG signal on the basis of the PWA scheme. The biometric sensor 230 may identify blood pressure information of a user (e.g. SBP and DBP) on the basis of a pulse wave velocity (PWV) scheme. The biometric sensor 230, in order to obtain blood pressure information of a user based on the PWV scheme, may further include at least one sensor (e.g., at least one electrode) for obtaining an electrocardiogram (ECG) signal, in addition to the PPG sensor. The processor 120 may identify the blood pressure information of a user (e.g., SBP and DBP) on the basis of the PPG sensor and the sensor for obtaining the ECG signal.

The processor 120 may identify information on the heart rate and/or a peak-to-peak interval (PPI) (e.g., a time interval) (hereinafter, which may be simply referred to as "PPI information" for the convenience of explanation) from the PPG signal obtained from the biometric sensor 230. Various kinds of techniques may be used for the method in which the processor 120 measures the heart rate and/or PPI information from the PPG signal obtained from the biometric sensor 230. The processor 120 may determine the degree of user's stress (e.g., a stress indicator) at least on the basis of the measured heart rate or PPI information. In the case where the electronic device 101 according to various embodiments includes an ECG electrode, it is also possible to identify the degree of stress using r-r interval (RRI) information, which is obtained using an ECG signal.

The processor 120 may utilize a PPG signal for calibration (hereinafter referred to as a "reference PPG signal") in order to identify the blood pressure information of a user. The reference PPG signal may be stored in the electronic device (e.g., the memory 130 in FIG. 1). The reference PPG signal may include one or more PPG signals. Blood pressure information corresponding to each of one or more reference PPG signals may be stored in the electronic device (e.g., the memory 130 in FIG. 1). For example, the electronic device (e.g., the memory 130 in FIG. 1) may store characteristic information of a waveform of the PPG signal {e.g., a peak value of the PPG signal (pulse wave), time intervals between the peaks, and the like}. The processor 120 may identify the characteristics of a biometric signal (e.g., a PPG signal) (hereinafter referred to by various names, such as "target biometric signal", "target PPG signal", or the like), which is obtained for measurement of biometric information (e.g., blood pressure). The processor 120 may identify the characteristics of a target PPG signal (e.g., the characteristics of a peak) by obtaining the second derivative of the target PPG signal. The processor 120 may compare the characteristics of a target PPG signal with the characteristics of a reference PPG signal, thereby estimating the current blood pressure of the user.

The reference PPG signal may include a single PPG signal and a single piece of blood pressure information corresponding to the single PPG signal. In this case, in order to identify (e.g., estimate) the blood pressure information from the target PPG signal, for example, the displacement of a feature point and the amount of change in the blood pressure corresponding to the displacement of the feature point may be stored in the form of a lookup table (LUT). The processor 120 may identify the displacement of at least one feature point of a target PPG signal and a reference PPG signal, and may obtain blood pressure information of a user on the basis of the information stored in the LUT. Alternatively, the amount of change in the blood pressure corresponding to the displacement of at least one feature point may be predetermined. The processor 120 may identify the displacement of at least one feature point of a target PPG signal and a reference PPG signal, and may apply a predetermined amount of change in the blood pressure, which corresponds to the identified displacement, to the reference PPG signal, thereby measuring the current blood pressure of the user. The reference PPG signal may include a plurality of PPG signals and blood pressure information corresponding to the respective PPG signals. In this case, the processor 120 may obtain blood pressure information of a user from the obtained target PPG signal using, for example, an interpolation method. According to various embodiments, various techniques for measuring the blood pressure of a user using the reference PPG signal and the target PPG signal may be applied.

The processor 120 may also obtain blood pressure information of a user on the basis of a PWV scheme. In this case, the electronic device 101 may include at least one electrode for obtaining an ECG signal. The processor 120 may obtain an image of the area around the user's face using an image-obtaining device (e.g., a normal camera or an IR camera), and may identify a change in the blood flow on the basis of a change in the color of the user's face included in the obtained image. The processor 120 may determine a pulse transit time of the blood flow required for the PWV scheme on the basis of the identified change in the blood flow. The processor 120 may calculate the pulse transit time of the blood flow required for the PWV scheme by measuring the ballistocardiogram (BCG) using an acceleration sensor.

The memory 130 may store a variety of data used for one or more elements (e.g., the processor 120, the motion sensor 220, or the biometric sensor 230) of the electronic device 101.

The touch screen display 200 may visually provide information to the outside (e.g., a user) of the electronic device 101. The touch screen display 200 may include a touch circuit configured to detect a touch or a sensor circuit (e.g., a pressure sensor) configured to measure the intensity of force generated by the touch.

The wireless communication circuit 210 may support the establishment of wireless communication channels between external electronic devices (e.g., the electronic device 102 in FIG. 1, the electronic device 104 in FIG. 1, or the server 108 in FIG. 1) and communications through the established wireless communication channels. The wireless communication circuit 210 may receive a variety of data (e.g., biometric information) from external electronic devices (e.g., the electronic device 102 in FIG. 1, the electronic device 104 in FIG. 1, or the server 108 in FIG. 1).

The motion sensor 220 may detect an operation state (e.g., motion) of the electronic device 101, and may produce an electrical signal or a data value corresponding to the detected state. The motion sensor 220 may include an acceleration sensor. The motion sensor 220 may include various kinds of sensors capable of detecting the motion of the electronic device 101.

The biometric sensor 230 may detect (e.g., obtain) biometric information of the user. The biometric information may include cardiovascular information such as arterial stiffness, blood pressure, arterial age, PPI information, RRI information, heart rate, and/or oxygen saturation in the blood. The biometric sensor 230 may include at least one light source (e.g., a light-emitting diode (LED)) having various wavelengths in order to obtain biometric information. The biometric sensor 230 may include a PPG sensor. The biometric sensor 230 (e.g., a PPG sensor) may obtain a PPG signal. The PPG signal may be obtained through the operation in which the biometric sensor 230 (e.g., a PPG sensor) detects the fluctuation of the optical signal corresponding to the volume change of the blood vessel. The PPG signal may refer to a signal obtained on the basis of a correlation between variation in the optical signal and the volume change of the blood vessel.

Figure 2B:
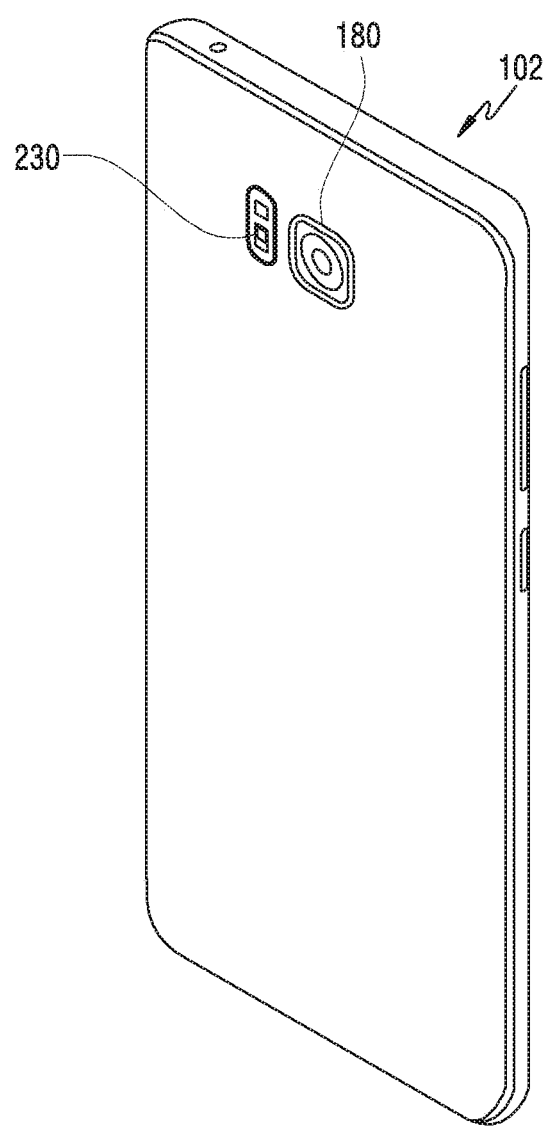
FIGS. 2B and 2C are diagrams for explaining an example of implementation of an electronic device having a biometric sensor provided therein according to various embodiments of the disclosure.
Figure 2C:
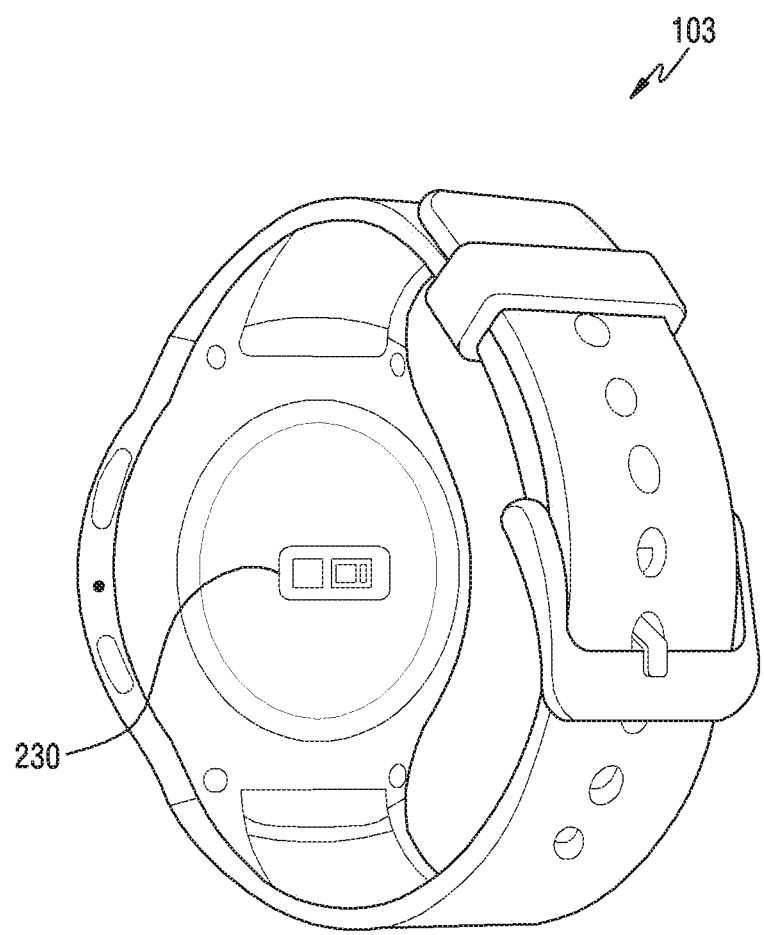

FIGS. 2B and 2C are diagrams for explaining an example of implementation of an electronic device having a biometric sensor provided therein according to various embodiments of the disclosure.

Referring to FIGS. 2B and 2C, the electronic device 101 may be implemented as a smart phone or a wearable device (e.g., a smart watch). For the sake of understanding, hereinafter, the electronic device implemented as a smart phone may be indicated by reference numeral 102, and the electronic device implemented as a wearable device may be indicated by reference number 103.

Referring to FIG. 2B, the electronic device 102 may be implemented as a smart phone. The biometric sensor 230 may be disposed in the back surface (e.g., the surface facing away from the surface in which the display is disposed) of the electronic device 102 (e.g., a smart phone). The biometric sensor 230 may be disposed adjacent to a camera module 180 (e.g., the camera module 180 in FIG. 1) in the back surface (e.g., the surface facing away from the surface in which the display is disposed) of the electronic device 102 (e.g., a smart phone).

Referring to FIG. 2C, the electronic device 103 may be implemented as a wearable device (e.g., a smart watch). The biometric sensor 230 may be disposed in the back surface (e.g., the surface facing away from the surface in which the display is disposed) of the electronic device 103 (e.g., a wearable device).

The biometric sensor (e.g., the biometric sensor 230 in FIG. 2A) may be disposed in a first portion of a housing of the electronic device 102 or 103.

Figure 2D:
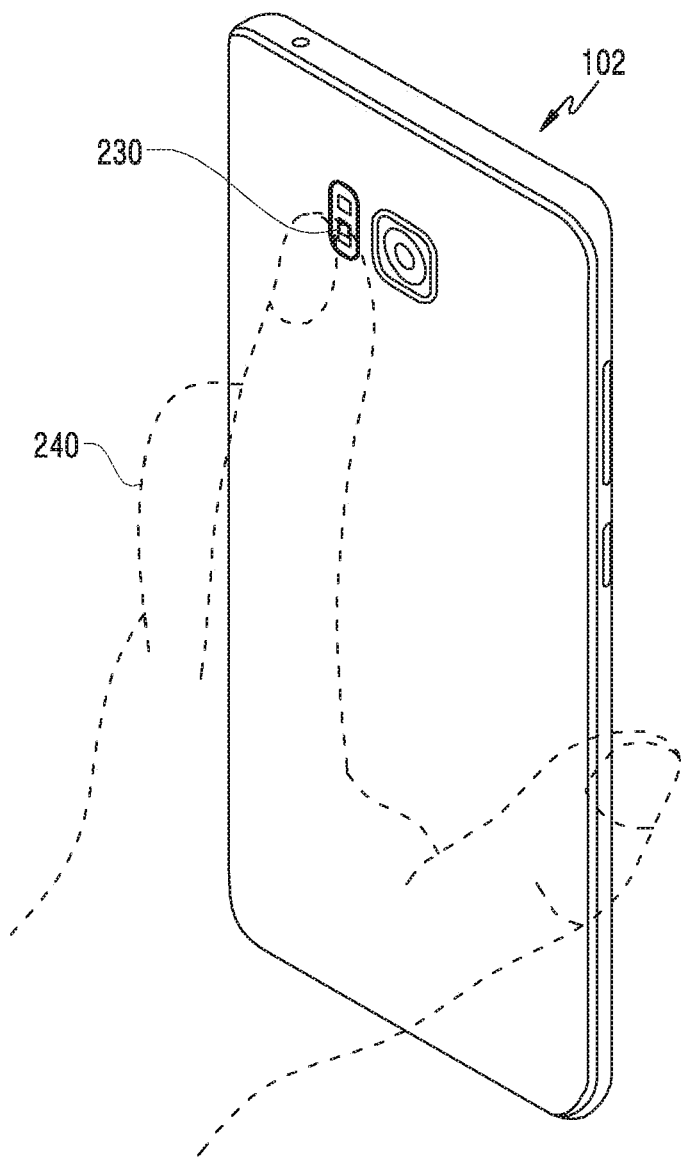
FIG. 2D is a diagram for explaining a method for obtaining biometric information through a biometric sensor of an electronic device according to an embodiment of the disclosure.

FIG. 2D is a diagram for explaining a method for obtaining biometric information through a biometric sensor of an electronic device according to an embodiment of the disclosure.

Referring to FIG. 2D, biometric information or a signal for identifying biometric information may be obtained by allowing a body part (e.g., a finger) of the user 240 to come into contact with the biometric sensor 230 or to approach the same. The biometric information or the signal for identifying biometric information may be obtained in various manners depending on the location of the biometric sensor 230 arranged in the electronic device 102.

Figure 3A:
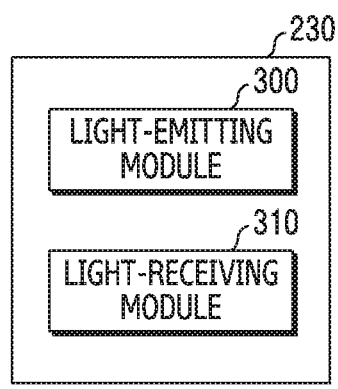
FIGS. 3A and 3B are diagrams for explaining a biometric sensor according to various embodiments of the disclosure.
Figure 3B:
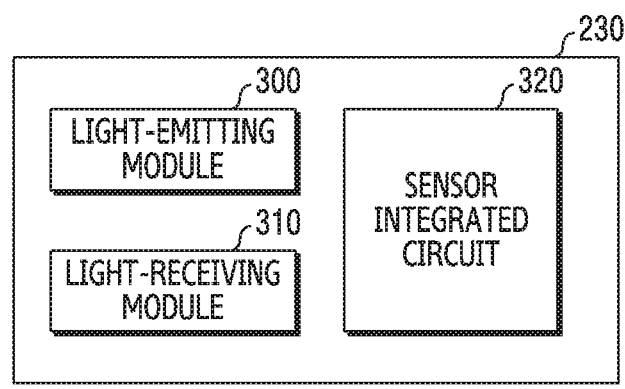

FIGS. 3A and 3B are diagrams for explaining the biometric sensor (e.g., the biometric sensor 230 in FIG. 2A) according to various embodiments of the disclosure.

Referring to FIG. 3A, the biometric sensor 230 (e.g., a PPG sensor) according to various embodiments may include a light-emitting module 300 and a light-receiving module 310.

The light-emitting module 300 may emit light to the outside in order to produce (e.g., obtain) a biometric signal (e.g., a PPG signal). The light-emitting module 300 may include at least one of a vertical cavity surface-emitting laser (VCSEL), a LED, a white LED, and a white laser. The light-emitting module 300 may include various kinds of light sources that emit light in various wavelength ranges (e.g., blue, green, red, and/or IR rays). The electronic device (e.g., the electronic device 101 in FIG. 1) may obtain a PPG signal using at least one of the various kinds of light sources. The light-emitting module 300 may emit light, which is modulated at a specific frequency, in order to produce a PPG signal.

The light-receiving module 310 may receive light that is emitted from the light-emitting module 300 and reflected by an object (e.g., a user). The light-receiving module 310 may convert the received light into an electrical signal. The light-receiving module 310 may produce a PPG signal using the received light. The light-receiving module 310 may include at least one of an avalanche photodiode (APD), a single photon avalanche diode (SPAD), a photodiode, a photomultiplier tube (PMT), a charge coupled device (CCD), a complementary metal-oxide-semiconductor (CMOS) array, and a spectrometer. The light-emitting module 300 may include various kinds of light sources that emit light in various wavelength ranges.

Referring to FIG. 3B, the biometric sensor 230 (e.g., a PPG sensor) may include a light-emitting module 300, a light-receiving module 310, and a sensor integrated circuit 320.

The sensor integrated circuit 320 may perform at least some of the functions performed by the processor (e.g., the processor 120 in FIG. 2A). The sensor integrated circuit 320 may be implemented as a single chip together with at least one of the light-emitting module 300 and the light-receiving module 310. The sensor integrated circuit 320 may also be implemented as a separate module from the light-emitting module 300 and the light-receiving module 310 so as to be operably connected to the light-emitting module 300 and the light-receiving module 310. The description related to FIG. 3A may also be applied to the light-emitting module 300 and the light-receiving module 310 according to various embodiments.

Figure 4:
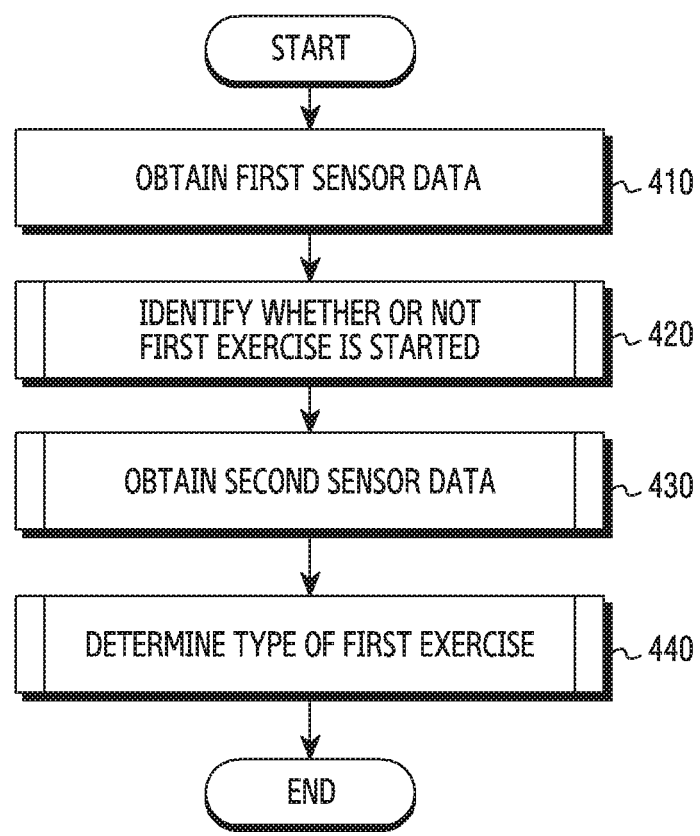
FIG. 4 is a diagram for explaining a method for determining the type of first exercise performed by a user in an electronic device according to an embodiment of the disclosure.

FIG. 4 is a diagram for explaining a method for determining the type of first exercise performed by a user in an electronic device (e.g., the electronic device 101 in FIG. 2A) according to an embodiment of the disclosure.

Referring to FIG. 4, the entity performing the operation may be an electronic device or a processor of an electronic device (e.g., the processor 120 in FIG. 2A). Hereinafter, for the convenience of explanation, the entity performing the operation will be described as an electronic device.

In operation 410, the electronic device may obtain first sensor data. The electronic device may obtain first sensor data using a first sensor.

The first sensor may be a sensor for detecting the motion of the electronic device. For example, the first sensor may be the motion sensor 220 shown in FIG. 2A. For example, the first sensor may be one of an acceleration sensor, a gyro sensor, or a proximity sensor.

The electronic device may obtain the first sensor data by activating the first sensor, which is in an inactive state. For example, the electronic device may activate the first sensor, which is in an inactive state, on the basis of a user input for executing a specific application (e.g., a healthcare application, or a fitness management application) installed in the electronic device. As another example, the electronic device may activate the first sensor, which is in an inactive state, on the basis of a user input for taking an image through a camera (e.g., the camera module 180 in FIG. 1). In another embodiment, the electronic device may also activate the first sensor, which is in an inactive state, in response to an operation of determining that the electronic device is currently in a specific location stored in the memory (e.g., the memory 130 in FIG. 1). The specific location may be the location of a fitness center (or gym) that is pre-registered by the user. As another example, the electronic device may also activate a specific application or the first sensor on the basis of reception of a user's voice input including information about the type of exercise (e.g., squat) and weight (e.g., 100 kg).

The electronic device may control the first sensor such that the first sensor remains in the active state even without user input while the electronic device is active. The electronic device may obtain first sensor data sensed by the first sensor in a specified cycle while the electronic device is active.

In operation 420, the electronic device may identify whether or not a first exercise has been started. "first exercise" may mean one set of exercises, or may mean one or more sets of exercises. One set means repeating a specific action one or more times without a break. For example, the first exercise may be performing a set of twelve squats. As another example, the first exercise may be performing five sets of twelve lateral raises.

The electronic device may determine whether or not the first exercise has been started on the basis of the first sensor data obtained in operation 410. The electronic device may determine whether or not the first exercise has been started or a start point of a time interval during which the first exercise is performed (hereinafter referred to as a "first time interval") in response to an operation of detecting that the obtained first sensor data value is equal to or greater than a first threshold value (or the obtained first sensor data is changed from a value less than the first threshold value to a value equal to or greater than the first threshold value). For example, in response to an operation of detecting that the first sensor data is changed from a value less than the first threshold value to a value equal to or greater than the first threshold value, the electronic device may determine that the user has started the first exercise, and may determine the time point at which the first sensor data is changed to a value equal to or greater than the first threshold value to be the start point of the first time interval.

In operation 430, the electronic device may obtain second sensor data. In an embodiment, the electronic device may obtain second sensor data using a second sensor. In an embodiment, the second sensor may be intended for detection of a biometric signal of the user. For example, the second sensor may be the biometric sensor 230 shown in FIG. 2A. The second sensor may be at least one of a PPG sensor and a heart rate sensor. The second sensor may include two or more sensors. For example, the second sensor may include both a PPG sensor and a heart rate sensor.

The second sensor data may be obtained irrespective of the acquisition of the first sensor data or on the basis of acquisition of the first sensor data.

For example, the electronic device may control the second sensor such that the second sensor remains in the active state while the electronic device is active. The second sensor may obtain a biometric signal of the user in a specified sensing cycle while the electronic device is active, and the electronic device may obtain the biometric signal of the user as the second sensor data. In this case, the second sensor data may be obtained irrespective of the acquisition of the first sensor data.

As another example, the electronic device may also obtain the second sensor data by activating the second sensor, which is in an inactive state, and may obtain the second sensor data by changing the configurations of the activated second sensor. In this case, a trigger operation of activating the second sensor, which is in an inactive state, or a trigger operation of changing the configurations of the activated second sensor (e.g., changing the sensing cycle of the second sensor from a first cycle to a second cycle, wherein the second cycle is shorter than the first cycle) may be a user input for activating the first sensor (e.g., a user input for executing a specific application) described in operation 410. In this case, the electronic device may obtain the second sensor data on the basis of acquisition of the first sensor data. However, the trigger operation of activating the second sensor, which is in an inactive state, or the trigger operation of changing the configurations of the activated second sensor may be separate user inputs from the user input for activating the first sensor described in operation 410. For example, the electronic device may activate the first sensor on the basis of a user input for executing a specific application, and may activate the second sensor, which is in an inactive state, on the basis of a user input for photographing images using a camera.

The second sensor data may be obtained irrespective of, or on the basis of, the determination of the start of the first exercise. For example, if the second sensor is configured to remain in the active state while the electronic device is active, the second sensor data may be obtained irrespective of the determination of the start of the first exercise. As another example, the electronic device may activate the second sensor, which is in an inactive state, or may change the configurations of the activated second sensor in response to the operation of determining that the first exercise has been started.

The first sensor data and the second sensor data obtained in operations 410 and 430 may be used to provide information about the exercise that has been performed by the user and the exercise that is to be performed by the user. Hereinafter, the exercise performed by the user will be referred to as "first exercise", and the exercise to be performed by the user will be described as "second exercise".

In operation 440, the electronic device may determine the type of the first exercise. For example, the electronic device may determine the type of the first exercise on the basis of at least some of the first sensor data or at least some of the second sensor data.

The type of first exercise may include at least one of types of exercise according to main categories (e.g., aerobic exercise, static exercise (muscular strength exercise), and the like) or types of exercise according to subcategories (e.g., squats, lateral raises, running, cycling, pushups, planks, etc.).

The electronic device may determine the type of first exercise according to the main categories on the basis of at least some of the first sensor data or at least some of the second sensor data. The second sensor data may include at least one piece of sensor data (e.g., at least one piece of blood pressure data and heart rate data or at least one of SBP, DBP, and mean arterial pressure (MAP), which are contained in the blood pressure data).

For example, the electronic device may determine the type of first exercise according to the main categories on the basis of at least some of the blood pressure data. The electronic device may determine the type of first exercise according to the main categories on the basis of a correlation between a plurality pieces of sensor data (SBP, DBP, MAP, etc.) included in the blood pressure data. For example, if the SBP, the DBP, and the MAP have a positive correlation in the first time interval (e.g., if all of the SBP, the DBP, and the MAP have increasing patterns), the electronic device may determine that the type of first exercise is static exercise (or muscular strength exercise). As another example, if the SBP and the DBP have a negative correlation or are decoupled from each other, the electronic device may determine that the type of first exercise is aerobic exercise. As another example, if a value indicating a positive correlation between the heart rate data and the blood pressure data is less than a specified value, the electronic device may determine that the type of first exercise is aerobic exercise.

The electronic device may determine the type of first exercise according to the subcategories on the basis of at least some of the first sensor data or at least some of the second sensor data.

The electronic device may determine the type of first exercise according to the subcategories using both at least some of the first sensor data and at least some of the second sensor data. In an embodiment, the electronic device may determine the type of first exercise according to the subcategories, taking into account the type of first exercise according to the main categories.

For example, if the first exercise is determined to be static exercise, and if the first sensor data during the first time interval shows a pattern that moves above a specified value in the vertical direction, the electronic device may determine that the type of the first exercise according to the subcategories is a squat. As another example, if the first exercise is determined to be static exercise, and if the first sensor data during the first time interval shows a pattern that moves below a specified value in the vertical direction, the electronic device may determine that the type of the first exercise according to the subcategories is a leg press. As another example, if the first sensor data during the first time interval is less than a specified value, and if the blood pressure data during the first time interval shows an increasing pattern, the electronic device may determine that the type of the first exercise is an exercise of holding the user's weight without moving the body (e.g., a "plank" core exercise).

Although it is not shown in the drawing, the electronic device may determine a variety of information about the first exercise (hereinafter referred to as "analysis information of the first exercise"), as well as the type of the first exercise. The electronic device may determine the analysis information of the first exercise by analyzing the first sensor data or the second sensor data. The analysis information of the first exercise may include information on at least one of the time during which the first exercise is performed, the intensity of the first exercise, the duration at the maximum exercise intensity, the number of repetitions of basic actions included in the first exercise, the number of calories consumed by the user performing the first exercise, and the amount of change in the blood pressure (or heart rate) of the user performing the first exercise. For example, the electronic device may determine information about the number of repetitions of basic actions (e.g., steps) included in the first exercise (e.g., running) using the first sensor data. The analysis information of the first exercise may include information about the type of the first exercise.

Figure 5:
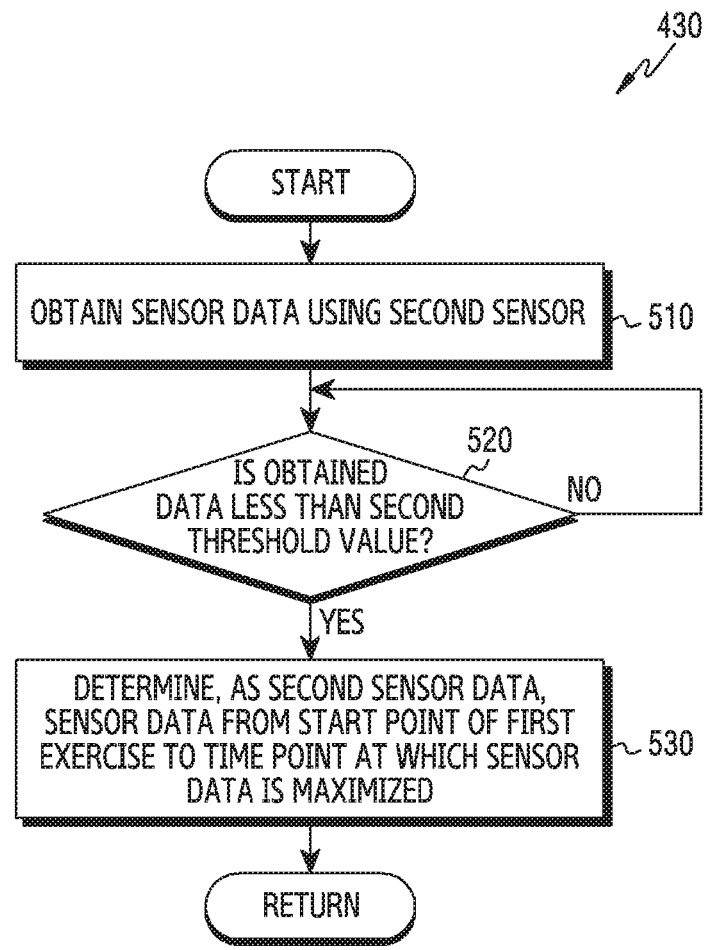
FIG. 5 is a diagram for explaining a method for obtaining second sensor data in order to determine the type of first exercise in an electronic device according to an embodiment of the disclosure.

FIG. 5 is a diagram for explaining a method for obtaining second sensor data in order to determine the type of first exercise in an electronic device (e.g., the electronic device 101 in FIG. 2A) according to an embodiment of the disclosure.

Referring to FIG. 5, the entity performing the operation shown in FIG. 5 may be an electronic device or a processor of an electronic device (e.g., the processor 120 in FIG. 2A). Hereinafter, for the convenience of explanation, the entity performing the operation will be described as an electronic device. FIG. 5 is a detailed flowchart of operation 430 illustrated in FIG. 4.

In operation 510, the electronic device may obtain sensor data using the second sensor. For example, the electronic device may obtain sensor data by activating the second sensor, which is in an inactive state.

In operation 520, the electronic device may determine whether or not the obtained sensor data value is below a second threshold value. If the obtained sensor data value is not below the second threshold value, the electronic device may repeat operation 510 and operation 520. If the obtained sensor data value is below the second threshold value, the electronic device may perform operation 530.

In operation 530, the electronic device may determine, as the second sensor data, the sensor data from the start point of the first exercise to the time point at which the sensor data is maximized. For example, the electronic device may determine the time point at which the sensor data is maximized between the start point of the first exercise and the time point at which the sensor data value is below the second threshold value, and may determine the time point at which the sensor data is maximized as an end point of the first exercise (or the end point of the first time interval).

The second threshold value may be a fixed value, or may change each time the user starts a new exercise. For example, the second threshold value may be determined on the basis of the second sensor data value at the start point of the first time interval, which is determined in operation 420. The second threshold value may be obtained by multiplying the second sensor data value at the start point of the first time interval by a specified ratio (e.g., 1.2 times).

The second threshold value may vary depending on the type of second sensor data. For example, if the second sensor data is blood pressure data, the second threshold value may be obtained by multiplying the second sensor data value at the start point of the first time interval by 1.2, and if the second sensor data is heart rate data, the second threshold value may be obtained by multiplying the second sensor data value at the start point of the first time interval by 1.5.

The electronic device may determine the first time interval during which the user performs the first exercise on the basis of the start point and the end point determined in operation 420 and operation 530.

The electronic device may determine the sensor data in the first time interval as the second sensor data. The electronic device may determine the sensor data obtained using the first sensor in the first time interval as the first sensor data.

Figure 6:
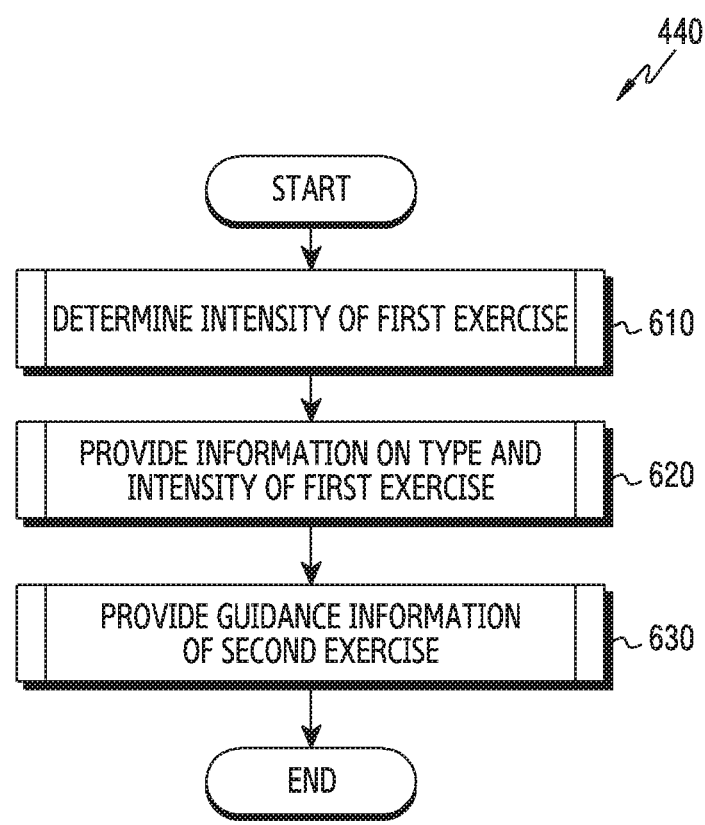
FIG. 6 is a diagram for explaining a method for providing second exercise guidance information in an electronic device according to an embodiment of the disclosure.

FIG. 6 is a diagram for explaining a method for providing second exercise guidance information in an electronic device (e.g., the electronic device 101 in FIG. 2A) according to an embodiment of the disclosure.

Referring to FIG. 6, the entity performing the operation shown in FIG. 6 may be an electronic device or a processor of an electronic device (e.g., the processor 120 in FIG. 2A). Hereinafter, for the convenience of explanation, the entity performing the operation will be described as an electronic device. FIG. 6 may be a detailed flowchart of operation 440 shown in FIG. 4.

In operation 610, the electronic device may determine the intensity of the first exercise. For example, the electronic device may determine the intensity of the first exercise before or after determining the type of the first exercise.

The electronic device may determine the intensity of the first exercise after the first exercise is complete. The electronic device may determine the intensity of the first exercise on the basis of at least one piece of the first sensor data and the second sensor data during the first time interval. The electronic device may also determine the intensity of the first exercise while the first exercise is being performed. The electronic device may determine the intensity of the first exercise on the basis of at least one piece of the first sensor data and the second sensor data from the start point of the first exercise to the present time.

The intensity of the first exercise may be a variable that indicates the ratio of the physical capacity, which was required for the first exercise performed by the user, compared to the maximum physical capacity of the user. The exercise intensity may be expressed as a numeral (e.g., percentage). The exercise intensity may vary depending on the user's physical ability, even for the same exercise. For example, when a squat is repeated 12 times with a weight of 30 kg, it may be relatively low exercise intensity for men in their twenties compared with women in their fifties. Therefore, the exercise intensity value for men in their twenties may be lower than the exercise intensity value for women in their fifties with respect to the above exercise.

The electronic device may determine the intensity of the first exercise on the basis of at least one of the maximum value of the second sensor data during the first time interval, the minimum value of the second sensor data, the difference between the maximum value and the minimum value, the average slope of the second sensor data during the first time interval, and the geometric characteristics of the second sensor data (e.g., the case where the slope of the second sensor data is changed at a specific point during the first time interval, and hereinafter, the specific point will be referred to as a "feature point").

The electronic device may determine the intensity of the first exercise using information about the type of the first exercise. For example, if the first exercise is determined to be aerobic exercise, the electronic device may assign a relatively high weight to the heart rate data and a relatively low weight to the blood pressure data, among the second sensor data, and if the second exercise is determined to be static exercise, the electronic device may assign a relatively low weight to the heart rate data and a relatively high weight to the blood pressure data. The electronic device may determine the intensity of the first exercise using the heart rate data and the blood pressure data that have different weights from each other. For example, if a weight of 80% is assigned to the heart rate data and a weight of 20% is assigned to the blood pressure data, among the second sensor data, a weight of 80% may be applied to at least one of the minimum value, the maximum value, the difference between the minimum value and the maximum value, and the average slope of the heart rate data, and a weight of 20% may be applied to at least one of the minimum value, the maximum value, the difference between the minimum value and the maximum value, and the average slope of the blood pressure data, thereby determining the intensity of the first exercise.

In operation 620, the electronic device may provide information about the type of first exercise and the intensity of the first exercise. The electronic device may provide information about the type of first exercise and the intensity of the first exercise in various forms or ways. For example, the electronic device may display information about the type and intensity of the first exercise on a display (e.g., the display device 160 in FIG. 1) on the basis of at least one of the determination or a user input, which indicates that the first exercise was finished. As another example, the electronic device may output information about the type and intensity of the first exercise to a speaker (e.g., the sound output device 155 in FIG. 1) on the basis of at least one of the determination or a user input indicating that the first exercise is finished. As another example, even before the first exercise is finished, the electronic device may provide the user with a warning (e.g., vibration or the like) that it may be better to stop the current exercise on the basis of the determination that the user is performing the first exercise with excessive strength or difficulty relative to the current physical capacity of the user.

Although not shown in the drawings, the electronic device may provide at least some of analysis information of the first exercise, which is obtained by analyzing the first sensor data or the second sensor data, as well as the information about the type and intensity of the first exercise. For example, the electronic device may further provide the user with information on at least one of the time during which the first exercise is performed, the duration at the maximum exercise intensity, the number of repetitions of basic actions included in the first exercise, the number of calories consumed by the user performing the first exercise, and the amount of change in the blood pressure (or heart rate) of the user performing the first exercise.

The electronic device may vary the information to be provided to the user depending on the type of the first exercise. For example, if the first exercise is static exercise, the electronic device may not provide information about the number of calories consumed by the user performing the first exercise. As another example, if the first exercise is aerobic exercise, the electronic device may not provide information about the amount of change in the blood pressure of the user performing the first exercise.

The electronic device may provide information about the type and intensity of the first exercise using a variety of output devices, such as a display (e.g., the display device 160), a speaker (e.g., the sound output device 155), a haptic module (e.g., the haptic module 179), and the like. For example, the electronic device may display, on the display, information about the type and intensity of the first exercise. The electronic device may display an exercise intensity value (e.g., percentage) on the display using various kinds of geometric objects (e.g., circles, ellipses, bar graphs, etc.). If the intensity value of the first exercise falls within a specified range (e.g., 90 to 100%), the electronic device may display information about the exercise intensity using a specific color (e.g., red). The electronic device may divide the entire range (e.g., 0 to 100%) into multiple ranges, and may display information about the exercise intensity by assigning different colors to the respective ranges. As another example, the electronic device may output information about the type and intensity of the first exercise through a speaker. For example, the electronic device may output voice information such as "10 squats with a weight of 40 kg have been performed. The exercise intensity thereof corresponds to 60%." through a speaker. As another example, the electronic device may transmit information about a specific sound (e.g., voice information) to another device through a communication circuit (e.g., the wireless communication circuit 210 in FIG. 2A or the communication module 190 in FIG. 1) so that the other device may output the specific sound through its own speaker. The other device may be connected to the electronic device using a short-range communication scheme (e.g., Bluetooth). For example, the other device may be a (wired or wireless) earphone device that is worn in the ears of the user.

In operation 630, the electronic device may provide guidance information on a second exercise. The second exercise may be an exercise that has not yet been performed by the user. The second exercise may be the exercise to be performed subsequent to the first exercise performed by the user.

The electronic device may provide guidance information on the second exercise to be performed by the user on the basis of at least one piece of analysis information of the first exercise (e.g., the type of exercise and the exercise intensity) and user input data.

The guidance information of the second exercise may indicate the most suitable exercise to be performed subsequently by the user in consideration of the user's exercise goal or the current physical condition of the user. For example, the guidance information of the second exercise may be one of the type of the second exercise according to main categories or subcategories, the intensity of the second exercise, a variable value of the second exercise to realize the intensity of the second exercise (e.g., the running speed or the angle of a treadmill in the case where the second exercise is running, the weight or the number of repetitions in the case where the second exercise is a squat, or the like), and a break time or an interval time before the start of the second exercise. For example, the electronic device may provide guidance information of the second exercise such as "You are recommended to perform 12 squats with a weight of 10 kg, heavier than the current weight, in 3 minutes". In the case where the electronic device provides information on the break time before the start of the second exercise, when the break time is over, the electronic device may inform the user that it is time to start the second exercise using one of the various kinds of output methods (e.g., vibration).

The electronic device may provide the guidance information of the second exercise (e.g., the intensity of the second exercise) on the basis of the analysis information of the first exercise. For example, if the intensity of the first exercise, among the analysis information of the first exercise, does not exceed a specified value (e.g., 80%), the electronic device may provide, as the intensity of the second exercise, a value obtained by increasing the intensity of the first exercise by a specified percentage (or a specified difference). As another example, if the intensity of the first exercise, among the analysis information of the first exercise, exceeds a specified value (e.g., 80%), the electronic device may provide, as the intensity of the second exercise, a value obtained by reducing the intensity of the first exercise by a specified percentage (or a specified difference). As another example, if the intensity of the first exercise, among the analysis information of the first exercise, falls within a specified range, the electronic device may provide a value, which is the same as the intensity of the first exercise or falls within a tolerance range thereof, as the intensity of the second exercise.

In an embodiment, the intensity of the second exercise may be implemented by one or more configuration values or variable values of the second exercise, and the electronic device may provide information about the configuration values or variable values of the second exercise, instead of the intensity of the second exercise, to realize the intensity of the second exercise. This is due to the fact that the numerical intensity of the second exercise may make it difficult for the user to intuitively perceive the intensity. For example, in the case where the user performed 10 squats with a weight of 30 kg (a first exercise), and if the intensity of the first exercise (e.g., 40%) is determined to be below a specified value (e.g., 50%), the electronic device may recommend the user to perform 12 squats with a weight of 40 kg (a second exercise) in order to realize exercise intensity of 60%, which is higher than the intensity of the first exercise.

The electronic device may provide guidance information of the second exercise (e.g., the type of second exercise) on the basis of the analysis information of the first exercise. For example, if the intensity of the first exercise, among the analysis information of the first exercise, does not exceed a specified value (e.g., 80%), the electronic device may directly provide, as the type of the second exercise, the type of the first exercise (e.g., squat). As another example, if the intensity of the first exercise, among the analysis information of the first exercise, exceeds a specified value (e.g., 80%), the electronic device may provide, as the type of the second exercise, a type of exercise (e.g., leg press or lunge) different from the type of the first exercise (e.g., squat). The electronic device may provide, as the type of the second exercise, a type of exercise related to the type of the first exercise (or related to the body parts moved in the first exercise) (e.g., squat→leg press or lunge, all of which are lower body exercises), or may provide, as the type of second exercise, a type of exercise unrelated to the type of the first exercise (e.g., squat→lateral raise, which is a shoulder exercise). For example, if the intensity of the first exercise is equal to or greater than a specified value (e.g., 90%), the electronic device may determine that the body part worked by the first exercise is almost out of strength, and may provide, as the type of the second exercise, a type of exercise unrelated to the type of first exercise.

The electronic device may provide guidance information of the second exercise on the basis of user input data. For example, the electronic device may provide the user with a user interface (e.g., a scroll bar) for receiving user feedback on the first exercise after (or while) providing information on the type and intensity of the first exercise in operation 620. The electronic device may receive information about the difficulty experienced by the user with respect to the first exercise through the user interface provided to the user. For example, the electronic device may receive numerical information about the difficulty experienced by the user with respect to the first exercise on the basis of a user input indicating a specific position using the scroll bar. If the user feedback on the exercise performed prior to the first exercise (hereinafter, referred to as a "third exercise") is stored in the memory, the electronic device may further display the user feedback on the third exercise while providing a user interface for receiving the user feedback on the first exercise, thereby allowing the user to determine the experienced difficulty (or experienced exercise intensity) of the first exercise relative to the third exercise. The user feedback on the third exercise may be displayed on the user interface for receiving the user feedback on the first exercise so as to overlap the same, or may be displayed in a separate area therefrom.

The electronic device may determine guidance information of the second exercise on the basis of the user feedback data on the first exercise. For example, if user input data stating that the first exercise was performed with an experienced difficulty (e.g., 90%) equal to or greater than a specified value (e.g., 80%) is received, the electronic device may provide guidance information of the second exercise in order to realize an exercise intensity less than 90%.

The electronic device may provide guidance information of the second exercise on the basis of both the analysis information of the first exercise and user input data. For example, the electronic device may apply predetermined weights to guidance information of the second exercise, which is determined using only the analysis information of the first exercise (first guidance information) and guidance information of the second exercise, which is determined using only the user input data (second guidance information), respectively, thereby determining the guidance information of the second exercise to be provided to the user. The electronic device may assign a relatively low weight to the first guidance information, and may assign a relatively high weight to the second guidance information, thereby determining the guidance information of the second exercise to be provided to the user. For example, the electronic device may determine the second guidance information itself as the guidance information of the second exercise to be provided to the user. For example, if the first guidance information denotes 8 squats with 60 kg and the second guidance information denotes 6 squats with 40 kg, the electronic device may provide 6 squats with 40 kg as the guidance information of the second exercise. As shown in the example described above, if the second guidance information itself is determined as the guidance information of the second exercise to be provided to the user (or the second guidance information is determined to be the guidance information of the second exercise by giving a relatively high weight thereto), the electronic device may further provide the first guidance information to the user. For example, the electronic device may further provide information such as "You can do 8 squats with 60 Kg in consideration of your current blood pressure data. Please give it a try!"

The user input data may be the data received through a user input for configuring an exercise goal, instead of the user feedback data on the first exercise. The user input for configuring the exercise goal may be input to the electronic device before performing the operation of obtaining the first sensor data (e.g., operation 410 in FIG. 4). The user input for configuring the exercise goal may be a user input by which the user configures the goal intended to be reached through the exercise. For example, the electronic device may provide a user interface for receiving the user input for configuring the exercise goal in response to a user input for executing a specific application (e.g., a healthcare application or a fitness application) installed in the electronic device (e.g., initial execution after installation). The electronic device may receive, through the user interface, information about at least one of a user's exercise goal (e.g., increasing muscular strength, increasing muscle endurance, losing weight, reducing body fat, training core muscles, etc.), a target period (1 month, 6 months, one year, etc.), and quantitative targets to be attained (increasing skeletal muscle by 1 kg, losing weight by 5 kg, reducing body fat by 4%, etc.). The electronic device may also receive information on a specific exercise scheme (e.g., a pyramid scheme, an inverted-pyramid scheme, an interval scheme, etc.) desired by the user through the user interface.

The electronic device may further receive the physical information of the user or exercise profile information through the user interface. For example, the electronic device may receive information about at least one of a user's age, height, weight, exercise history, medical history (e.g., hypertension, etc.) through the user interface. The electronic device may determine the exercise level of the user on the basis of the received physical information or exercise profile information of the user. As another example, the electronic device may obtain normal blood pressure or heart rate information of the user using the second sensor. The electronic device may also store information received through the user interface or information obtained through the second sensor in the memory (e.g., the memory 130 in FIG. 1). Although not shown in the drawings, the electronic device may also separately provide information for efficient attainment of the configured exercise goal.

The electronic device, in response to the reception of a user input for configuring the exercise goal, may provide information for efficient attainment of the configured exercise goal through the user interface. For example, if the user wishes to exercise with the goal of losing weight, the electronic device may provide the user with information about the most efficient exercise routine for losing weight. As another example, if the user wishes to exercise with the goal of increasing muscular strength, the electronic device may provide the user with information about the most efficient exercise routine for increasing muscular strength. The information about the exercise routine may include information on a division scheme, at least one type of exercise and exercise sequence (e.g., squat→leg press→lunge), a distribution scheme of the exercise intensity (e.g., a pyramid or inverted-pyramid scheme), and a recommended exercise time. For example, if the user wishes to exercise with the goal of increasing muscular strength, the electronic device may propose a three-divisional exercise scheme (a scheme in which all body parts are divided into three groups, thereby exercising in a cycle of three days), and may propose an exercise routine for performing squats, leg presses, and dumbbell lunges for the lower body in an inverted pyramid scheme of the three-divisional exercise scheme.

The electronic device may further provide the user with relevant information or link information of the related video such that the user may check the postures of the squat, leg press, and dumbbell lunge. When providing the user with information for efficient attainment of the configured exercise goal, the electronic device may further inform the user that the exercise guidance information (e.g., guidance information of the second exercise) to be provided to the user in the future will be determined on the basis of the information for efficient attainment of the configured exercise goal. For example, if the difficulty or exercise intensity experienced by the user for the first exercise (five squats with 30 kg) exceeds a specified value (e.g., 80%), the electronic device may suggest that the user perform the leg press rather than the squat on the basis of the information for efficient attainment of the configured exercise goal (e.g., lower-body routine information indicating squat→leg press→lunge).

In the case where the embodiment disclosed in FIG. 4 is performed by the electronic device 103, the information about the type and intensity of the first exercise provided in operation 620 and the guidance information of the second exercise provided in operation 630 may be produced by the electronic device 102.

Figure 7:
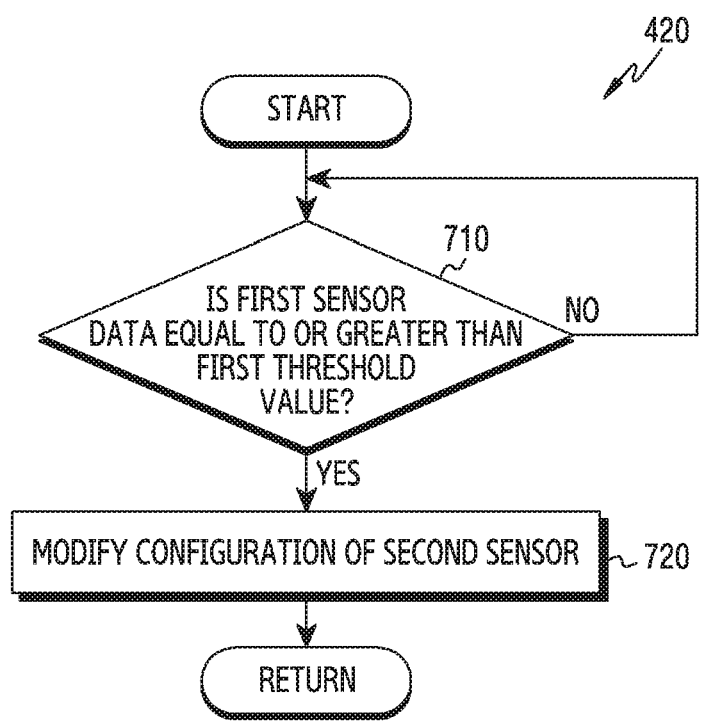
FIG. 7 is a diagram for explaining a method for identifying whether or not a first exercise performed by the user has been started in an electronic device according to an embodiment of the disclosure.

FIG. 7 is a diagram for explaining a method for identifying whether or not the first exercise performed by the user has been started in an electronic device (e.g., the electronic device 101 in FIG. 2A) according to an embodiment of the disclosure.

Referring to FIG. 7, the entity performing the operation may be an electronic device or a processor of an electronic device (e.g., the processor 120 in FIG. 2A). Hereinafter, for the convenience of explanation, the entity performing the operation will be described as an electronic device.

In operation 710, the electronic device may detect whether or not the first sensor data value obtained through the activated first sensor is equal to or greater than a first threshold value, or whether or not the first sensor data has changed from a value less than the first threshold value to a value equal to or greater than the first threshold value, thereby determining that the user has started the first exercise.

The electronic device may detect whether or not the first sensor data obtained through the activated first sensor repeatedly becomes a value less than the first threshold value and a value equal to or greater than the first threshold value in a periodic pattern, thereby determining that the user has started the first exercise. This is due to the fact that most muscular strength exercises include repetition of specific actions (e.g., sitting and standing in the case of the squat), wherein the first sensor data is detected to be equal to or greater than the first threshold value while the specific actions are being performed, but the first sensor data is detected to be less than the first threshold value at the time at which the specific actions are terminated.

If it is determined that the user has not yet started the first exercise, the electronic device may perform operation 710 again. That is, the electronic device may repeat operation 710 until it is determined that the user has started the first exercise.

If it is determined that the user has started the first exercise, the electronic device may change the configuration of the second sensor in operation 720. If the first sensor data is determined to be equal to or greater than the first threshold value, the electronic device may determine that the user has started the first exercise, thereby changing the configuration of the second sensor.

The electronic device may change the configuration related to activation of the second sensor. For example, the electronic device may activate the second sensor, which is in an inactive state.

The electronic device may change the configuration related to a sensing cycle of the second sensor that is in the active state. For example, the electronic device may switch the sensing cycle of the second sensor from a first cycle to a second cycle.

Although not shown in the drawings, the electronic device may determine that the user has terminated the first exercise on the basis of the first sensor data or the second sensor data. For example, the electronic device may determine that the user has terminated the first exercise if the second sensor data value is less than a specified value. On the basis of the determination that the user has terminated the exercise, the electronic device may switch the second sensor from the active state to the inactive state, or may switch the sensing cycle of the activated second sensor from the second cycle to the first cycle. As a result, the electronic device may obtain more accurate and detailed sensing data for the time interval (first time interval) during which the user is actually performing the exercise.

Figure 8A:
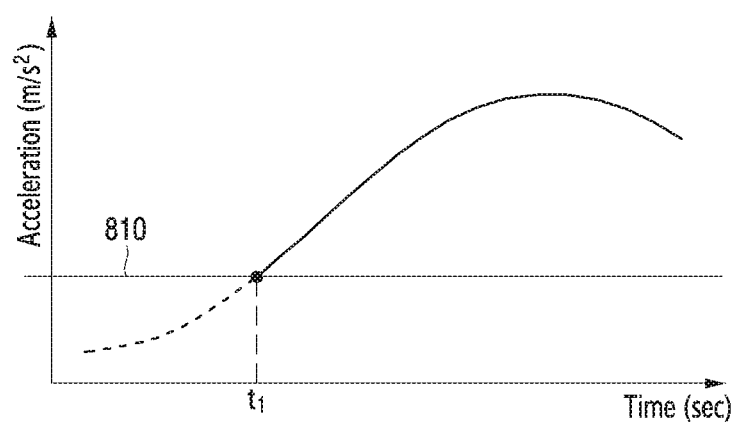
FIGS. 8A and 8B are diagrams of first sensor data according to various embodiments of the disclosure.
Figure 8B:
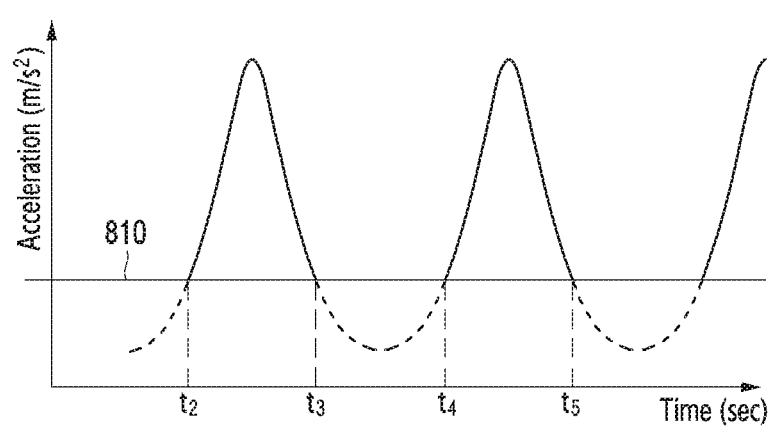

FIGS. 8A and 8B are diagrams of the first sensor data according to various embodiments of the disclosure.

Referring to FIGS. 8A and 8B, the first sensor data may be expressed by a graph in which the x-axis represents time (unit: sec) and the y-axis represent acceleration (unit: m/s^2).

The electronic device may determine that the user has started the first exercise on the basis of detection of that the first sensor data value exceeds a first threshold value 810. The electronic device may also determine that the user has started the first exercise on the basis of detection that the first sensor data repeatedly goes up and down above and below the first threshold value 810 more than a predetermined number of times (e.g., twice).

Referring to FIG. 8A, on the basis of detection that the first sensor data value exceeds the first threshold value 810, the electronic device may determine the point (e.g., t1) at which the first sensor data value exceeds the first threshold value 810 to be the start point of the first time interval during which the user performs the first exercise.

Referring to FIG. 8B, on the basis of detection that the first sensor data repeatedly goes up and down above and below the first threshold value 810 more than a predetermined number of times, the electronic device may determine the point (e.g., t2) at which the first sensor data value exceeds the first threshold value for the first time as the start point of the first time interval during which the user performs the first exercise.

Figure 9A:
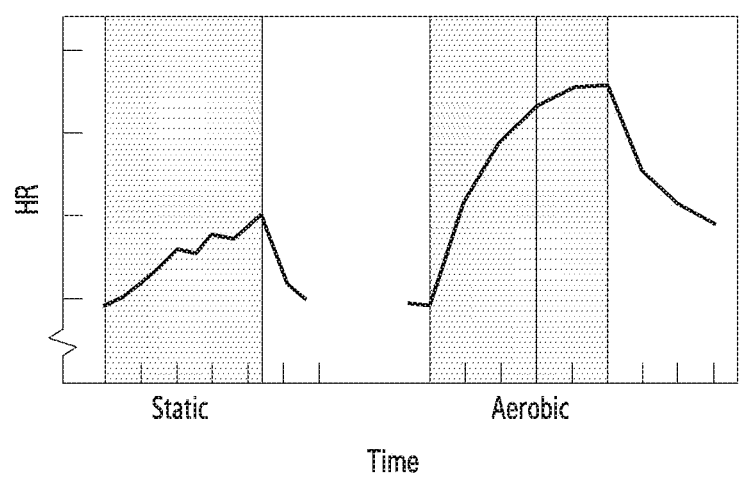
FIGS. 9A and 9B are diagrams of second sensor data according to various embodiments of the disclosure.
Figure 9B:
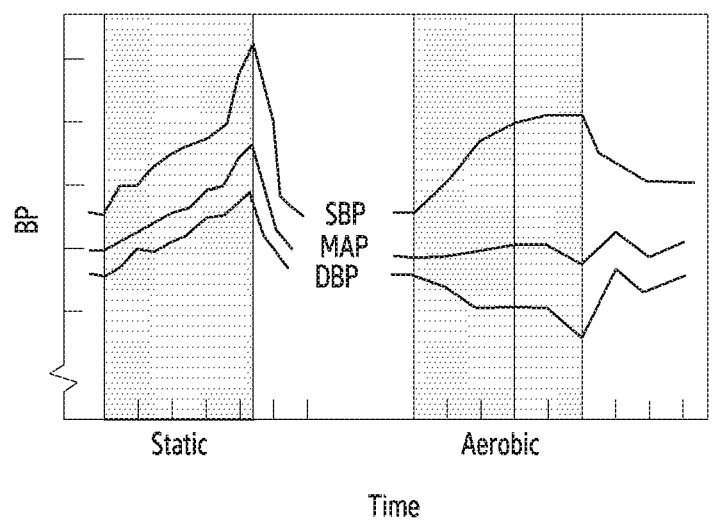

FIGS. 9A and 9B are diagrams of the second sensor data according to various embodiments of the disclosure.

Referring to FIGS. 9A and 9B, the second sensor data may include heart rate data and blood pressure data.

FIG. 9A shows variation in a heart rate (or a variation pattern) depending on time in the case static exercise and aerobic exercise are respectively performed, and FIG. 9B shows variation of blood pressure (or a variation pattern) depending on time in the case static exercise and aerobic exercise are respectively performed. Referring to FIG. 9A, it can be seen that the heart rate data increases more highly and more sharply during the aerobic exercise than during the static exercise. Accordingly, if the exercise intensity is determined on the basis of the heart rate data, the accurate exercise intensity may not be provided to the user. In order to compensate for this, blood pressure data may be used. Referring to FIG. 9B, it can be seen that the variation pattern of blood pressure data is different for the aerobic exercise and the static exercise. Specifically, blood pressure data increases more highly and more steeply during the static exercise than during the aerobic exercise. In addition, all of three types of data (e.g., SBP, MAP, and DMP) included in the blood pressure data exhibit increasing patterns during the static exercise rather than the aerobic exercise. The electronic device may provide appropriate guidance for the intensity of the first exercise performed by the user and the intensity of the second exercise to be performed by the user using at least one piece of the heart rate data and the blood pressure data according to the type of exercise performed by the user.

Figure 10:
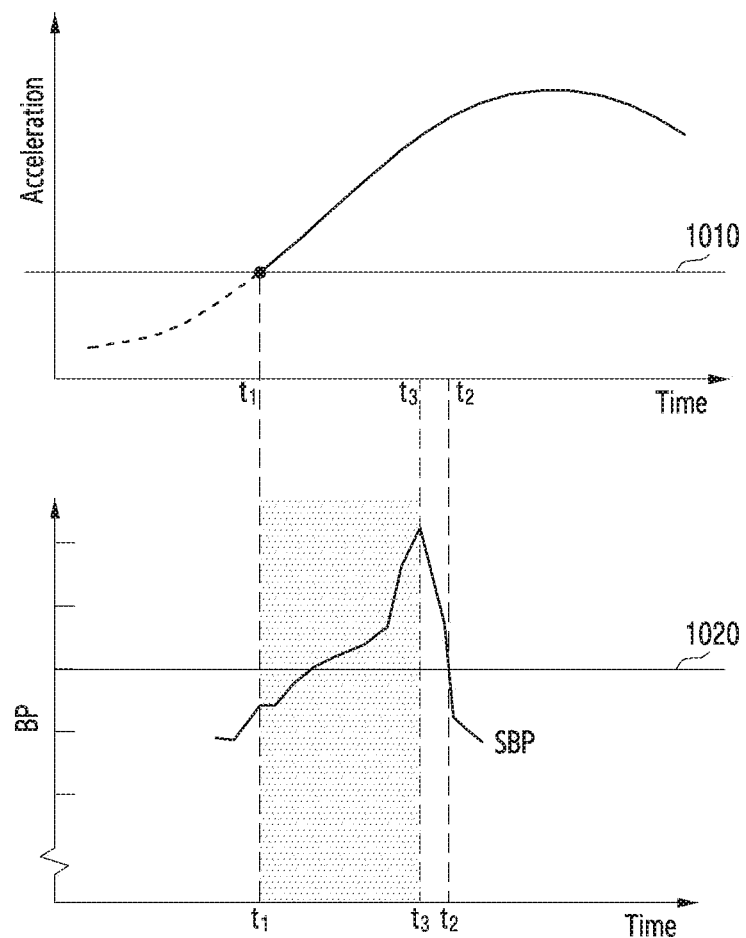
FIG. 10 is a diagram illustrating an example of determining a first time interval according to an embodiment of the disclosure.

FIG. 10 is a diagram illustrating an example of determining a first time interval according to an embodiment of the disclosure.

Referring to FIG. 10, the first graph shows the first sensor data, and the second graph shows the second sensor data (in particular, the SBP of the blood pressure data). The two graphs may share the same time axis.

Referring to the first graph in FIG. 10, the electronic device, in response to the operation of detecting that the first sensor data is changed from a value less than a first threshold value 1010 to a value equal to or greater than the first threshold value 1010, may determine that the user has started the first exercise, and may determine the time point (e.g., t1) at which the first sensor data is changed to the value equal to or greater than the first threshold value 1010 to be the start point of the first time interval.

Referring to the second graph in FIG. 10, the electronic device, in response to the operation of detecting that the second sensor data is changed from a value equal to or greater than a second threshold value 1020 to a value less than the second threshold value 1020, may determine that the user has terminated the first exercise. The electronic device may determine the time point (e.g., t3) at which the second sensor data has the maximum value between the start point (e.g., t1) of the first time interval and the time point (e.g., t2) at which the second sensor data is changed to the value less than the second threshold value. The electronic device may determine the time point (e.g., t3) at which the second sensor data has the maximum value to be the end point of the first time interval.

The second threshold value may be determined on the basis of the second sensor data value at the start point of the first time interval.

Although only the SBP of the second sensor data is shown in the drawing, the embodiment may be applied to the MAP and the DBP in the same manner, and it is obvious that at least two of SBP, MAP, and DBP may be considered.

Figure 11:
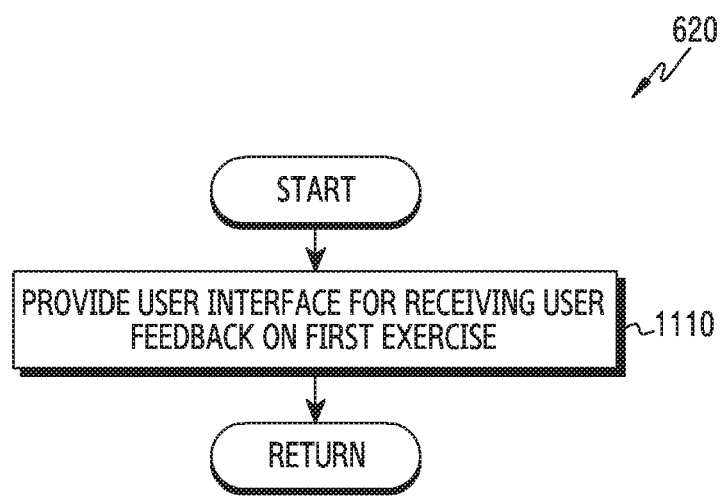
FIG. 11 is a diagram for explaining a method for providing the type and the intensity of a first exercise performed by a user in an electronic device according to an embodiment of the disclosure.

FIG. 11 is a diagram for explaining a method for providing the type and intensity of the first exercise performed by a user in an electronic device (e.g., the electronic device 101 in FIG. 2A) according to an embodiment of the disclosure.

Referring to FIG. 11, the entity performing the operation shown in FIG. 11 may be an electronic device or a processor of an electronic device (e.g., the processor 120 in FIG. 2A). Hereinafter, for the convenience of explanation, the entity performing the operation will be described as an electronic device. FIG. 11 is a detailed flowchart of operation 620 in FIG. 6.

In operation 1110, the electronic device may provide a user interface for receiving user feedback on the first exercise.

The electronic device 102 may provide (e.g., display) a user interface (e.g., display touch, a keyboard, voice input, etc.) on the basis of the reception of a signal in relation to provision of a user interface from the electronic device 103. In addition, the electronic device 103 may provide a user interface on the basis of reception of a signal in relation to provision of a user interface from the electronic device 102.

The electronic device may provide a user interface for receiving user feedback on the first exercise at the same time as (or after) analysis information of the first exercise (e.g., information on the type of first exercise, the intensity of the first exercise, and the like) is provided.

The analysis information of the first exercise may include values for a plurality of items, and the user interface may include various kinds of objects that allow the user to change a value for at least one of the plurality of items. For example, although the electronic device determines that the type of the first exercise is a squat and that the number of basic actions included in the first exercise is 10 and provides information thereabout, if the user actually performs 12 squats, the user may change the information so as to correspond to the fact that 12 squats have been performed by manipulating the user interface. As another example, although the electronic device determines that the intensity of the first exercise is 60%, if the user determines that the intensity of the first exercise is relatively higher than 60%, the user may change the intensity of the first exercise by manipulating the user interface.

Figure 12:
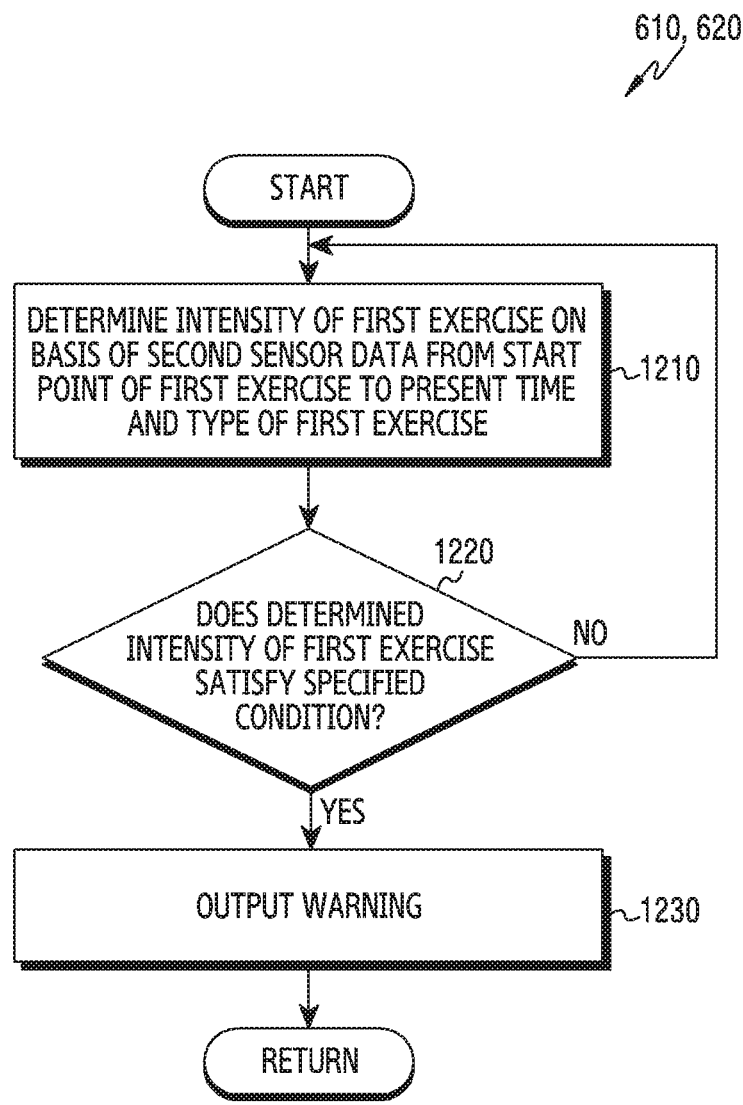
FIG. 12 is a diagram for explaining a method for outputting a warning on the basis of the type and the intensity of a first exercise performed by a user in an electronic device according to an embodiment of the disclosure.

FIG. 12 is a diagram for explaining a method for outputting a warning, on the basis of the type and intensity of the first exercise performed by a user, from an electronic device (e.g., the electronic device 101 in FIG. 2A) according to an embodiment of the disclosure. FIG. 12 is a detailed flowchart of operations 610 and 620 in FIG. 6.

FIG. 12 shows an embodiment of providing a warning (or notification) to the user if analysis information of the first exercise that is performed so far (e.g., the intensity of the first exercise) satisfies a specified condition in the state in which the first exercise is not yet terminated.

In operation 1210, the electronic device may determine the intensity of the first exercise on the basis of the second sensor data from the start point of the first exercise (e.g., the time point at which the first sensor data value is equal to or greater than the first threshold value) to the current time and the identified type of the first exercise. For example, the electronic device may determine the intensity of the first exercise on the basis of the minimum value, the maximum value, the difference between the minimum value and the maximum value, and the average slope of the second sensor data from the time point at which the first sensor data is equal to or greater than the first threshold value to the current time.

In operation 1220, the electronic device may identify whether or not the intensity of the first exercise determined in operation 1210 satisfies a specified condition. If it is identified that the intensity of the first exercise determined in operation 1210 does not satisfy the specified condition, the electronic device may perform operation 1210 again. The electronic device may re-perform operation 1210 by re-identifying the second sensor data from the time point at which the first sensor data is equal to or greater than the first threshold value to the current time. If it is identified that the intensity of the first exercise determined in operation 1210 satisfies the specified condition, the electronic device may output a warning (or notification) in operation 1230.

The specified condition may be predetermined in order to inform the user that the user needs to stop the first exercise that is being performed in consideration of the current state of the user. For example, the specified condition may include a condition in which the intensity value of the first exercise is equal to or greater than a predetermined threshold value (e.g., 90%).

The electronic device may identify whether or not the variation in the second sensor data itself follows a specified pattern, as well as whether or not the intensity of the first exercise determined on the basis of the second sensor data satisfies a specified condition.

In operation 1230, the electronic device may output a warning or notification in any of various forms. For example, the electronic device may output a warning or notification that advise the user to stop the current exercise using various kinds of output devices, such as a display (e.g., the display device 160), a speaker (e.g., the sound output device 155), a haptic module (e.g., the haptic module 179), and the like.

Although not shown in the drawings, the electronic device may further provide a user interface for receiving user feedback after outputting a warning in operation 1230. For example, if the electronic device detects that the user has terminated the first exercise after outputting a warning in operation 1230, the electronic device may further provide a user interface for receiving user feedback on the first exercise.

Although not shown in the drawings, the electronic device may also output a warning if at least some of the second sensor data obtained from the time point at which the first sensor data is equal to or greater than the first threshold value to the time is equal to or greater than a specified value. For example, the specified value may be determined on the basis of a user's medical history (e.g., hypertension). In this case, the electronic device may output a warning in response to the operation of detecting that at least some of the second sensor data is equal to or greater than the specified value even if the type or the intensity of the first exercise is not determined.

Figure 13:
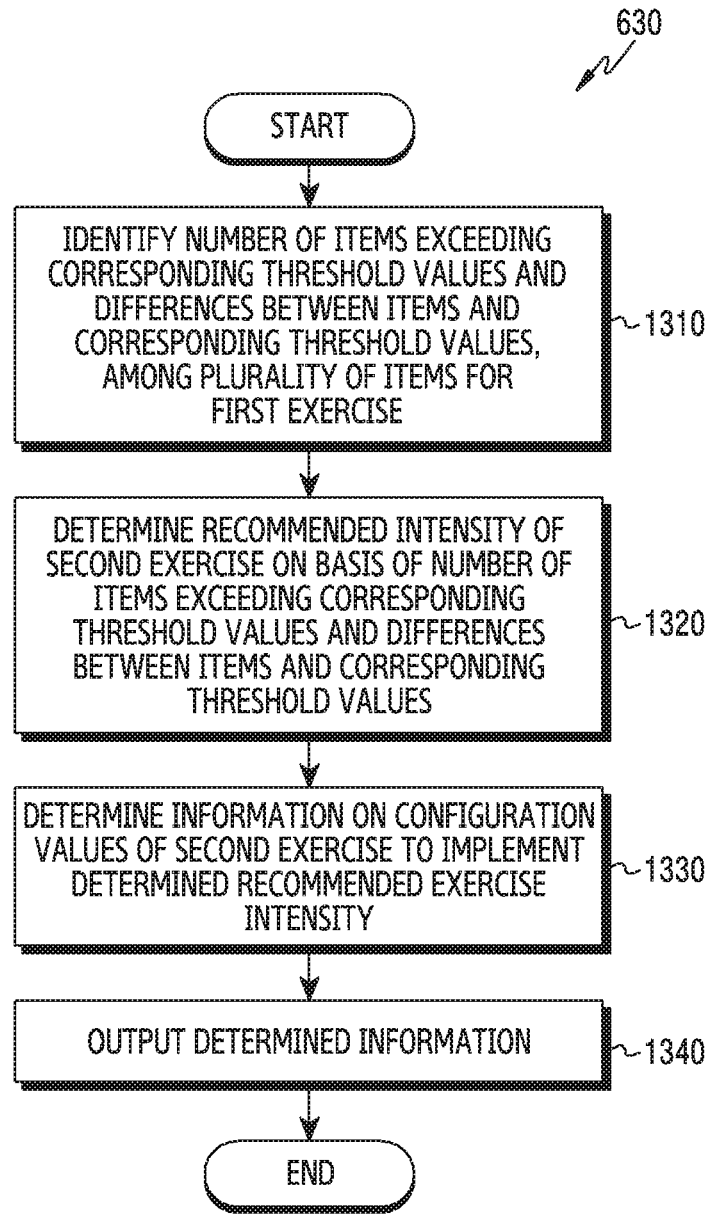
FIG. 13 is a diagram for explaining a method for providing second exercise guidance information in an electronic device according to an embodiment of the disclosure.

FIG. 13 is a diagram for explaining a method for providing second exercise guidance information in an electronic device (e.g., the electronic device 101 in FIG. 2A) according to an embodiment of the disclosure.

Referring to FIG. 13, FIG. 13 is a detailed flowchart of operation 630 in FIG. 6.

In operation 1310, the electronic device may identify the number of items that exceed corresponding threshold values and the differences between the items and the corresponding threshold values, among a plurality of items for the first exercise.

The plurality of items for the first exercise may include items associated with the second sensor data, which is used to determine the intensity of the first exercise. For example, the plurality of items for the first exercise may include at least one of the minimum value, the maximum value, the difference between the minimum value and the maximum value, and the average slope of the second sensor data during the first time interval.

The electronic device may identify the number of items that exceed the corresponding threshold values, among the plurality of items for the first exercise. The electronic device may pre-store threshold values corresponding to the respective items in the memory (e.g., the memory 130 in FIG. 1). The electronic device may learn the threshold values corresponding to the respective items such that the difference between the intensity of the first exercise determined by the electronic device (first exercise intensity) and the intensity of the first exercise determined (or experienced) by the user (second exercise intensity) is reduced as the user repeats the embodiment of the disclosure. The threshold values corresponding to the respective items, which are stored in the electronic device, may be adjusted on the basis of the physical characteristics and the exercise levels of the user of the electronic device. The threshold values corresponding to the respective items, which are stored in the electronic device, may vary depending on the type of exercise. For example, the difference between the minimum value and the maximum value of the blood pressure data during the first time interval, among the second sensor data, may correspond to a threshold value of 60 (mmHg) for static exercise and 40 (mmHg) for aerobic exercise. As another example, the average slope of the blood pressure data during the first time interval, among the second sensor data, may correspond to a threshold value of 15 (mmHg/s) for static exercise and 12 (mmHg/s) for aerobic exercise. If the difference between the minimum value and the maximum value of the blood pressure data is 63 (mmHg) and the average slope thereof is 20 (mmHg/s), among the second sensor data, during the first time interval, and if the type of first exercise is static exercise, the electronic device may identify that the number of items that exceed the corresponding threshold values is two or more.

The electronic device may identify the differences between the items exceeding the corresponding threshold values and the corresponding threshold values. For example, the electronic device may identify information in which the difference between the minimum value and the maximum value is greater than the threshold value by 3 (mmHg), and may identify information in which the average slope is greater than the threshold value by 5 (mmHg/s).

In operation 1320, the electronic device may determine the recommended intensity of the second exercise on the basis of the number of items exceeding the corresponding threshold values and the differences between the items and the corresponding threshold values.

The electronic device may determine the recommended intensity of the second exercise, which is different from the intensity of the first exercise. For example, if the number of items exceeding the corresponding threshold values is zero, the electronic device may set the recommended intensity of the second exercise to an exercise intensity (e.g., 70%) greater than the intensity of the first exercise (e.g., 60%). As another embodiment, if the number of items exceeding the corresponding threshold values is more than a specified number, the electronic device may set the recommended intensity of the second exercise to an exercise intensity (e.g., 70%) less than the intensity of the first exercise (e.g., 80%). The ratio of the intensity of the first exercise to the recommended intensity of the second exercise or the difference between the intensity of the first exercise and the recommended intensity of the second exercise may be determined according to the number of items exceeding the corresponding threshold values and the differences between the items and the corresponding threshold values.

In operation 1330, the electronic device may determine the configuration values (or variable values) of the second exercise in order to realize the recommended intensity of the second exercise. For example, if the user has performed 10 squats with a weight of 30 kg as the first exercise, and if the recommended intensity of the second exercise (70%) was determined to be less than the intensity of the first exercise (80%), the electronic device may determine to perform 8 squats with a weight of 25 kg in order to realize the recommended intensity of the second exercise. As another example, if the user has performed 10 squats with a weight of 30 kg as the first exercise, and if the recommended intensity of the second exercise (80%) was determined so as to be greater than the intensity of the first exercise (70%), the electronic device may determine to perform 10 squats with a weight of 40 kg, or may determine to perform 12 squats with a weight of 30 kg in order to realize the recommended intensity of the second exercise. As another example, if the first exercise was performed 40 seconds after the completion of the third exercise, and if the recommended intensity of the second exercise (80%) was determined so as to be less than the intensity of the first exercise (90%), the electronic device may determine to perform the second exercise 60 seconds after the first exercise in order to realize the recommended intensity of the second exercise.

In an embodiment, configuration values of the second exercise to implement the recommended intensity of the second exercise may be determined on the basis of the information used to determine the recommended intensity of the second exercise. For example, if the items exceeding the corresponding threshold values are related to the heart rate data, instead of the blood pressure data, the electronic device may change the weight while maintaining the number of repetitions. As another example, if the items exceeding the corresponding threshold values are related to the blood pressure data, the electronic device may change the number of repetitions while maintaining the weight.

In another embodiment, the configuration values of the second exercise for implementing the recommended intensity of the second exercise may be determined on the basis of user input data. For example, the configuration values of the second exercise may be determined on the basis of the exercise goals configured by the user. If the user is exercising for the purpose of increasing muscular strength, the electronic device may change the weight while maintaining the number of repetitions.

In operation 1340, the electronic device may output the determined information. For example, the electronic device may display, on the display, a guidance message such as "You are recommended to perform 10 squats with a weight of 40 kg next".

Figure 14:
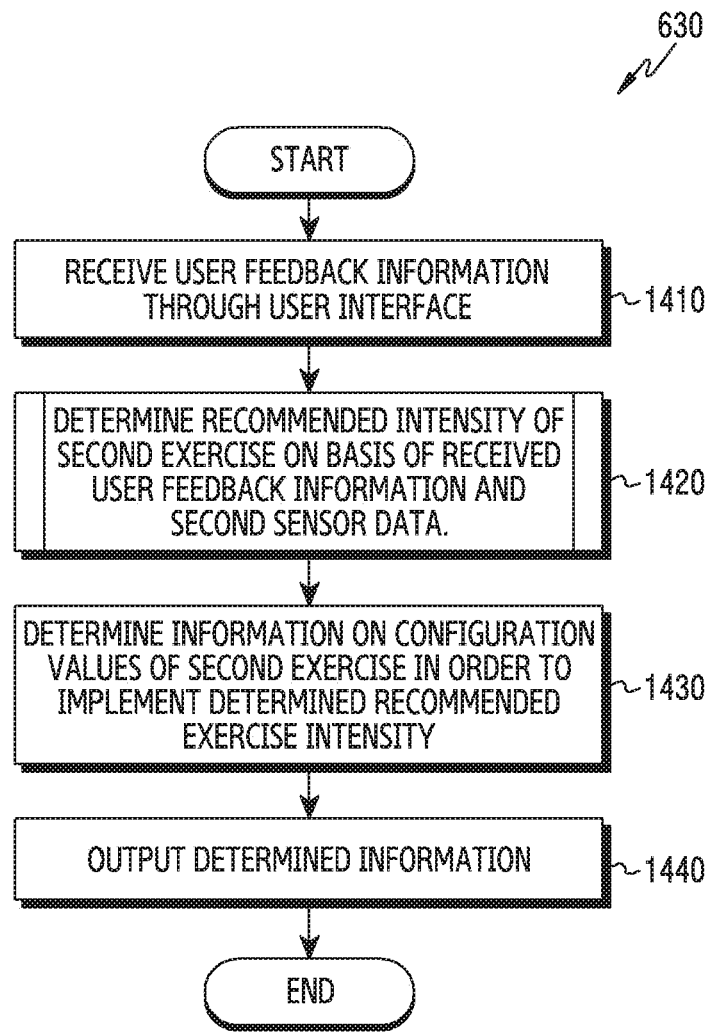
FIG. 14 is a diagram for explaining a method for providing second exercise guidance information in an electronic device according to an embodiment of the disclosure.

FIG. 14 is a diagram for explaining a method for providing second exercise guidance information in an electronic device (e.g., the electronic device 101 in FIG. 2A) according to an embodiment of the disclosure.

Referring to FIG. 14, FIG. 14 is a detailed flowchart of operation 630 shown in FIG. 6.

Unlike the embodiment in FIG. 13 in which the recommended intensity of the second exercise is determined on the basis of the second sensor data, FIG. 14 shows an embodiment in which the recommended intensity of the second exercise is determined on the basis of the second sensor data and user feedback data.

In operation 1410, the electronic device may receive user feedback information through a user interface. The electronic device may receive user feedback information through a user interface for receiving user feedback on the first exercise, which is provided in operation 1110 in FIG. 11.

Figure 20:
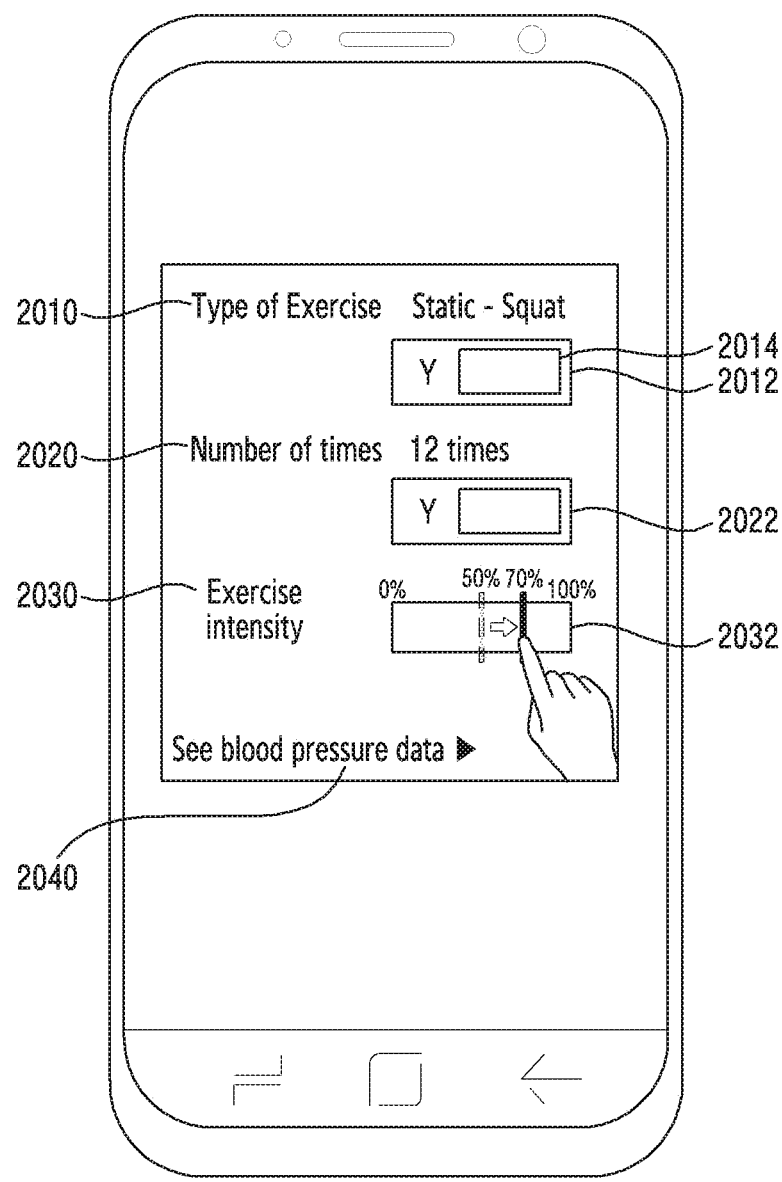
FIG. 20 is a diagram illustrating a user interface for analysis information of a first exercise according to an embodiment of the disclosure.

FIG. 20 is a diagram illustrating a user interface for analysis information of a first exercise according to an embodiment of the disclosure The user interface for receiving user feedback on the first exercise is shown in FIG. 20.

Referring to FIG. 20, analysis information of the first exercise (e.g., the type of first exercise, the exercise intensity, etc.) may be provided to the user, and the analysis information of the first exercise may include a plurality of items 2010, 2020, and 2030. For example, the electronic device may display, on a display (e.g., the display device 160 in FIG. 1), an exercise category item 2010 and a value for the item determined by the electronic device (e.g., "static exercise—squat"). In an embodiment, the electronic device may further provide an object 2040 for identifying the second data that was used to determine the analysis information of the first exercise.

In an embodiment, the electronic device may display, on the display, objects 2012, 2022, and 2032 for modifying the information for the respective items 2010, 2020, 2030, which is determined by the electronic device.

For example, the object 2012 for modifying information about the type of exercise may include a sub-object 2014, and if the sub-object is touched, the electronic device may further display an input window for receiving correct information about the type of exercise from the user. The electronic device may modify the value for the exercise category item 2010 on the basis of a user input entered into the input window. If the value for the exercise category item 2010 is modified on the basis of the user input entered into the input window, the electronic device may store, in a memory (e.g., the memory 130 in FIG. 1), the modified information so as to be mapped with the first sensor data during the first time interval and the second sensor data thereof. The mapping information stored in the memory may be referred to or used by the electronic device in order to determine the type of the exercise to be perform next by the user.

As another example, the object 2032 for modifying (or re-entering) information on the exercise intensity may include a sliding bar capable of moving in a specific direction (e.g., to the left and right). The electronic device may determine the initial position of the sliding bar (e.g., 50%) to be the position corresponding to the first exercise intensity determined by the electronic device. The electronic device may receive information about the second exercise intensity (70%) experienced by the user on the basis of a user input for moving the sliding bar in a specific direction, and may modify the value for the exercise intensity item 2030.

Although not shown in the drawings, the electronic device may receive user feedback information using a microphone (e.g., the input device 150 in FIG. 1). For example, the electronic device may receive user voice data such as "weight 40 kg, a little bit hard, about 70%" through the microphone. The electronic device may analyze and parse the received voice data to determine information about the weight of the first exercise and information about the second exercise intensity. In the case where the embodiment shown in FIG. 14 is performed by the electronic device 103, the electronic device 103 may receive, from another electronic device (e.g., the electronic device 102 or wired/wireless earphones (not shown)), user voice data that is received by another electronic device. In the case where the embodiment shown in FIG. 14 is performed by the electronic device 102, the electronic device 102 may receive, from another electronic device (e.g., wired/wireless earphones (not shown)), user voice data that is received by another electronic device.

Referring back to FIG. 14, in operation 1420, the electronic device may determine the recommended intensity of the second exercise on the basis of the received user feedback information and the second sensor data. The electronic device may determine the recommended intensity of the second exercise on the basis of the received user feedback information. For example, if the electronic device receives the second exercise intensity (e.g., 90%) that falls within a specified range, the electronic device may determine the recommended intensity of the second exercise to be lower than the second exercise intensity.

The electronic device may determine the recommended intensity of the second exercise on the basis of both the received user feedback information and the second sensor data. For example, the electronic device may determine the recommended intensity of the second exercise by considering both the second exercise intensity according to the user feedback information and the first exercise intensity according to the second sensor data. The electronic device may determine the recommended intensity of the second exercise by applying predetermined weights to the second exercise intensity and the first exercise intensity, respectively. For example, if the difference between the first exercise intensity value and the second exercise intensity value is within a specified range, one of either the first exercise intensity or the second exercise intensity may be determined as the recommended intensity of the second exercise.

Since operations 1430 to 1440 are the same as or similar to operations 1330 to 1340 in FIG. 13, a detailed description thereof will be omitted.

Figure 15:
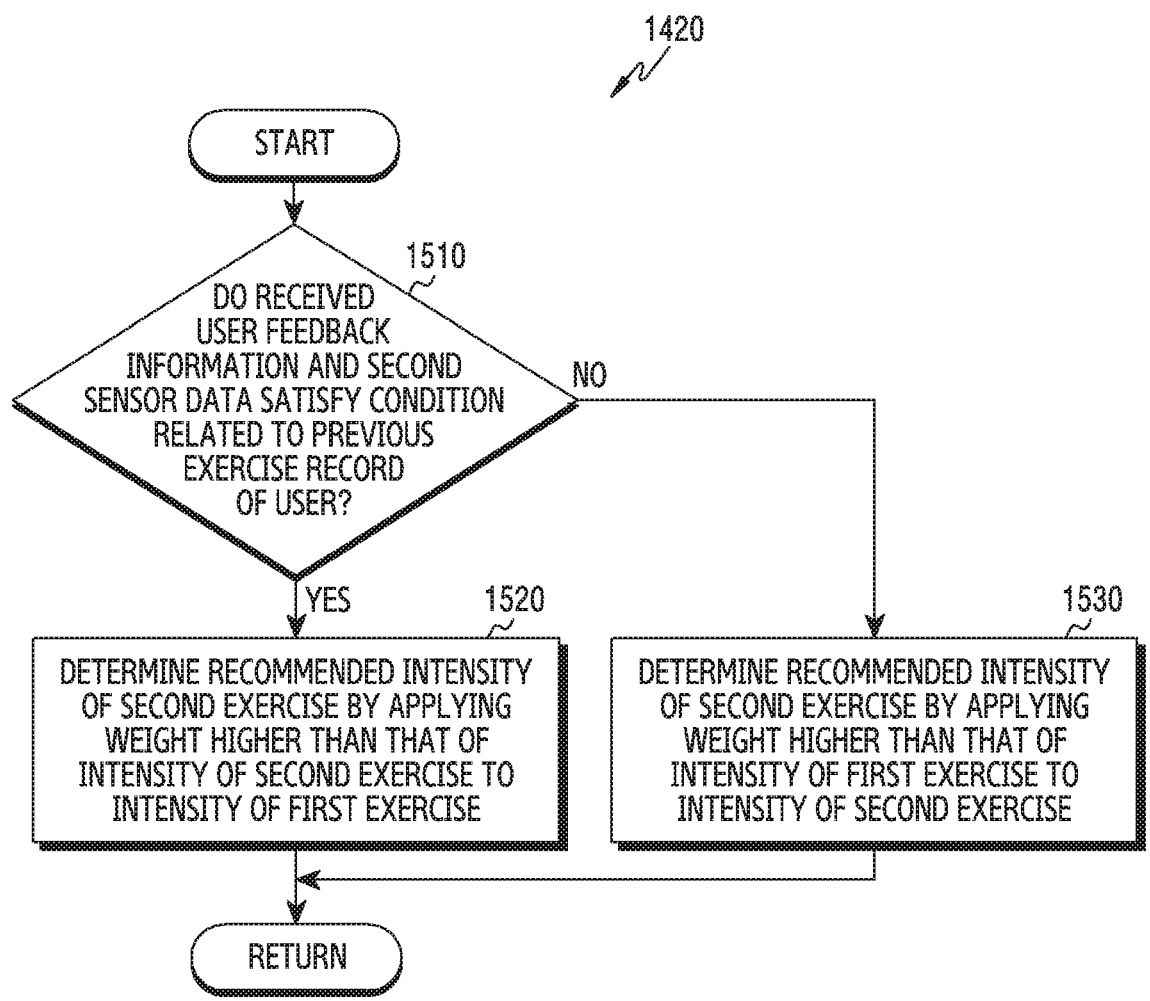
FIG. 15 is a diagram for explaining a method for determining the recommended exercise intensity of a second exercise in an electronic device according to an embodiment of the disclosure.

FIG. 15 is a diagram for explaining a method for determining the recommended intensity of the second exercise in an electronic device (e.g., the electronic device 101 in FIG. 2A) according to an embodiment of the disclosure.

Referring to FIG. 15, FIG. 15 is a detailed flowchart of operation 1420 shown in FIG. 14.

In operation 1510, the electronic device may identify whether or not the received user feedback information and the second sensor data satisfy a condition related to the previous exercise record of the user.

The electronic device may generally assign, to the second exercise intensity associated with the user feedback information, a weight higher than that of the first exercise intensity associated with the second sensor data. For example, the electronic device may determine the second exercise intensity as the recommended intensity of the second exercise. This is due to the fact that the first exercise intensity associated with the second sensor data may not correctly reflect the user's particular circumstances (e.g., drinking, hangover, sleeplessness, bad condition, the case where the user has weaker muscles and joints than normal people, the case where the user feels pain in a specific body part when performing the first exercise, or the like) because it relies on a limited amount of sensor data. However, if the received user feedback information and the second sensor data satisfy specific conditions, the electronic device may perform operation 1520. The electronic device may determine the recommended intensity of the second exercise by applying a weight higher than that of the second exercise intensity to the first exercise intensity. If the received user feedback information and the second sensor data do not satisfy specific conditions, the electronic device may perform operation 1530. The electronic device may determine the recommended intensity of the second exercise by applying a weight higher than that of the first exercise intensity to the second exercise intensity.

The specific condition may be related to the previous exercise record of the user. The previous exercise record of the user may be stored in the memory (e.g., the memory 130 in FIG. 1). The previous exercise record of the user may include second sensor data and user feedback data for the previous time that the user performed exercise. For example, the electronic device may retrieve the number of times the first exercise intensity is lower than the second exercise intensity from the sensor data similar to the second sensor data obtained in operation 420, and if the retrieved number of times is equal to or greater than a specified number, the electronic device may determine that the user has more potential, and may assign a weight higher than that of the second exercise intensity to the first exercise intensity. For example, the electronic device may determine the first exercise intensity as the recommended intensity of the second exercise.

Although not shown in the drawings, the specific condition may not be related to the previous exercise record of the user. For example, if the second exercise intensity associated with the user feedback information is greater than the first exercise intensity associated with the second sensor data, and if the difference therebetween falls within a specified range, the electronic device may determine that the user has more potential, and may assign a weight higher than that of the second exercise intensity to the first exercise intensity.

In the case where a weight higher than that of the second exercise intensity is assigned to the first exercise intensity, the electronic device, when outputting guidance information of the second exercise thereafter (e.g., operation 1440 in FIG. 14), may further output information stating that the output guidance information of the second exercise was determined by assigning a weight higher than that of the second exercise intensity to the first exercise intensity and that the guidance information of the second exercise was determined by assigning a higher weight to the second exercise intensity or was determined on the basis of the second exercise intensity.

In operation 1520, the electronic device may determine the recommended intensity of the second exercise by assigning a weight relatively higher than that of the second exercise intensity to the first exercise intensity.

In operation 1530, the electronic device may determine the recommended intensity of the second exercise by assigning a weight relatively higher than that of the first exercise intensity to the second exercise intensity.

Figure 16:
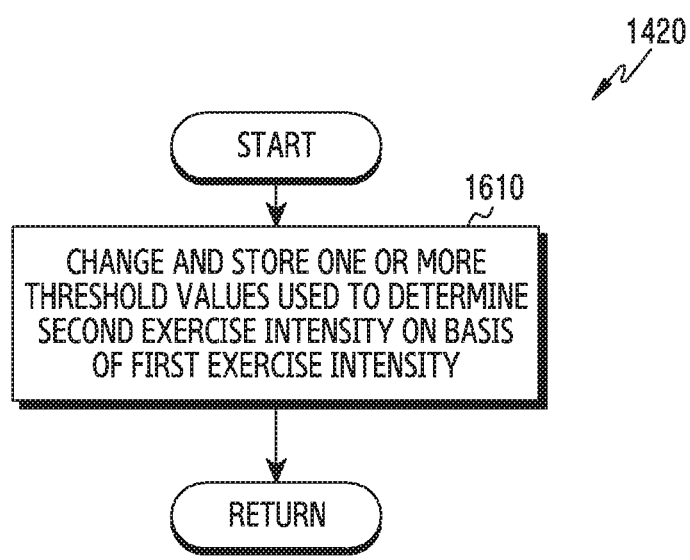
FIG. 16 is a diagram for explaining a method for determining the recommended exercise intensity of a second exercise in an electronic device according to an embodiment of the disclosure.

FIG. 16 is a diagram for explaining a method for determining the recommended exercise intensity of the second exercise in an electronic device (e.g., the electronic device 101 in FIG. 2A) according to an embodiment of the disclosure.

Referring to FIG. 16, FIG. 16 is a detailed flowchart of operation 1420 shown in FIG. 14.

In operation 1610, the electronic device may change and store one or more threshold values used to determine the first exercise intensity value on the basis of the second exercise intensity value. The electronic device may change and store one or more threshold values, which were used to determine the first exercise intensity value, such that the difference between the first exercise intensity value and the value of the second exercise is reduced, instead of determining the recommended intensity of the second exercise on the basis of the second exercise intensity value. For example, if the first exercise intensity value is 70% and the second exercise intensity value is 80%, the electronic device may change one or more threshold values (e.g., the difference between the minimum value and the maximum value of the second sensor data, the average slope of the second sensor data during the first time interval, and the like), which were used to determine the first exercise intensity value, and may store the changed values in the memory (e.g., the memory 130 in FIG. 1), instead of determining the recommended intensity of the second exercise on the basis of the second exercise intensity value 70%. When changing one or more threshold values, which were used to determine the first exercise intensity value, if there is a log by which one or more threshold values have previously been changed, the electronic device may use the log. The log may include information showing the one or more threshold values before and after the change and a change in the difference between the first exercise intensity value and the second exercise intensity value before and after the change.

Figure 17:
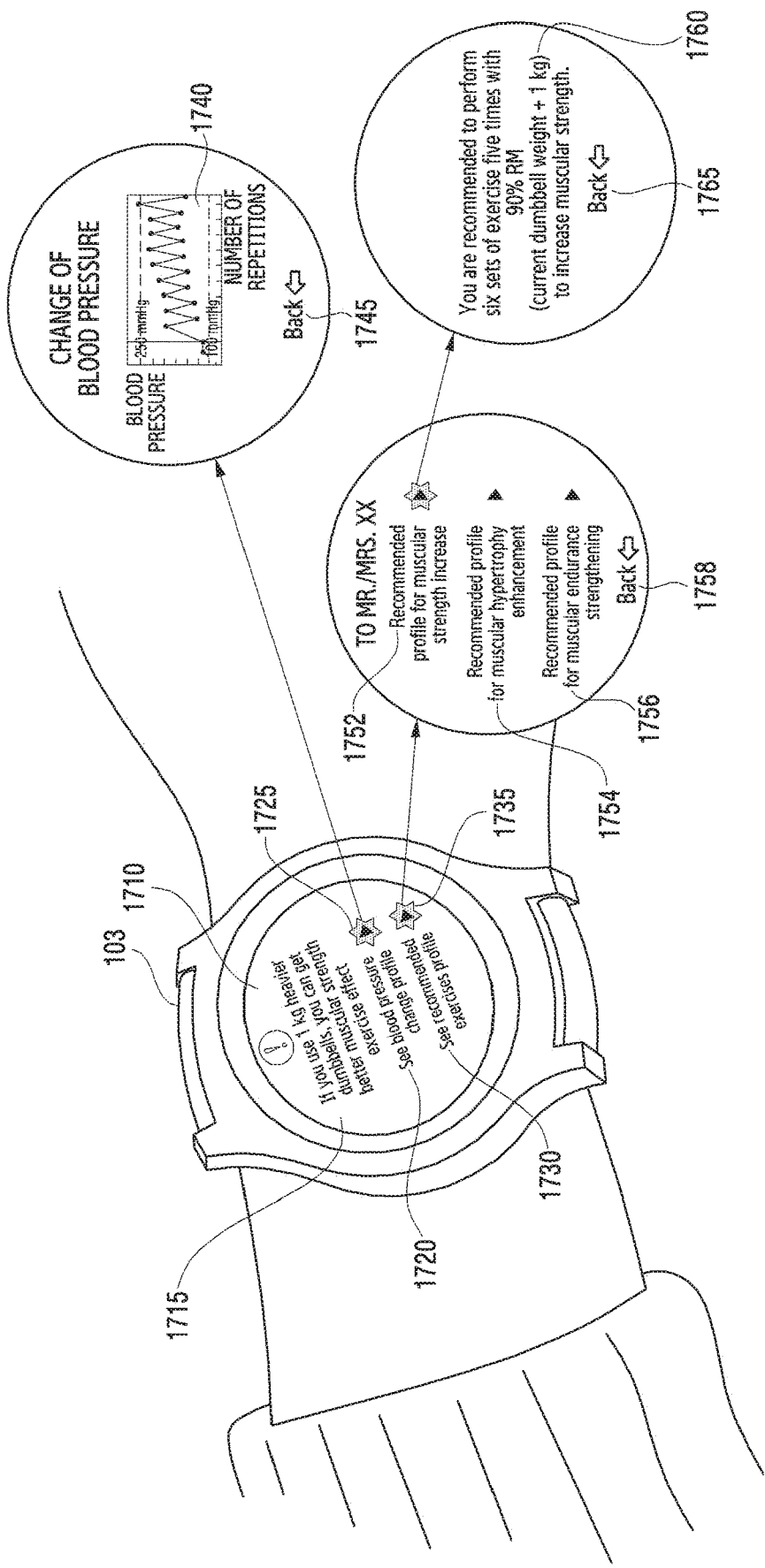
FIG. 17 is a diagram of a user interface displayed in an electronic device according to an embodiment of the disclosure.

FIG. 17 is a diagram of a user interface displayed in an electronic device (e.g., the electronic device 101 in FIG. 2A) according to an embodiment of the disclosure.

Referring to FIG. 17, the electronic device 103 is a watch-type wearable device, and FIG. 17 shows the electronic device 103 worn on the user's wrist.

The user interface 1710 displayed on the electronic device 103 may be intended to output information about configuration values of the second exercise (see operation 1340 in FIG. 13) in order to realize the recommended intensity of the second exercise.

The user interface 1710 displayed on the electronic device 103 may include guidance text 1715 for configuration values of the second exercise, guidance text 1720 for displaying the second sensor data during the first time interval on the basis of user input, and guidance text 1730 for displaying more detailed configuration values of the second exercise. An object 1725 for receiving user input may be displayed in the area adjacent to the guidance text 1720, and an object 1735 for receiving a user input may be displayed in the area adjacent to the guidance text 1730.

The electronic device may display sensor data 1740 for the first time interval on the basis of a user input with respect to the object 1725. Although FIG. 17 shows only the blood pressure data as an example of the sensor data, this is merely an example, and it will be obvious to those skilled in the art that any amount of the first sensor data and the second sensor data may be displayed. In an embodiment, the electronic device may replace the currently displayed screen with a screen in which the sensor data in the first time interval is displayed, or may display the sensor data in a portion of the currently displayed screen so as to overlap the same on the basis of a user input with respect to the object 1725. In the case where the currently displayed screen is replaced with a screen in which the sensor data in the first time interval is displayed, an object 1745 for receiving a user input for making a request to return to the previous screen may be further displayed.

The electronic device may further display more detailed configuration values of the second exercise on the basis of a user input to the object 1735. For example, the electronic device may further display guidance text 1760, such as "You are recommended to exercise five times in six sets with 1 kg added to current dumbbell weight" and a back button 1765. As another example, the electronic device may display a screen for receiving a user input for selecting any one of a variety of exercise goals, and may receive a user input for selecting any one of a variety of exercise goals, thereby further displaying more detailed configuration values of the second exercise. For example, the screen for receiving a user input for selecting one of a variety of exercise goals may display objects 1752, 1754, and 1756 related to an increase in the muscular strength, enhancement of muscular hypertrophy, and strengthening of muscular endurance, respectively, and a back button 1758.

FIGS. 18A to 18D illustrate an example of sensor data used to determine whether or not to make a request for stopping the first exercise according to various embodiments of the disclosure.

Figure 18A:
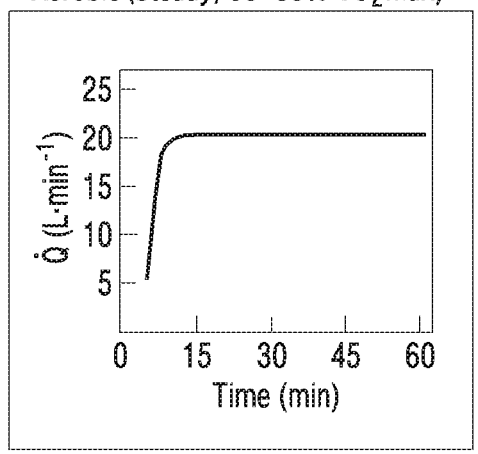
FIGS. 18A, 18B, 18C, and 18D illustrate an example of sensor data used to determine whether or not to make a request for stopping a first exercise according to various embodiments of the disclosure.
Figure 18B:
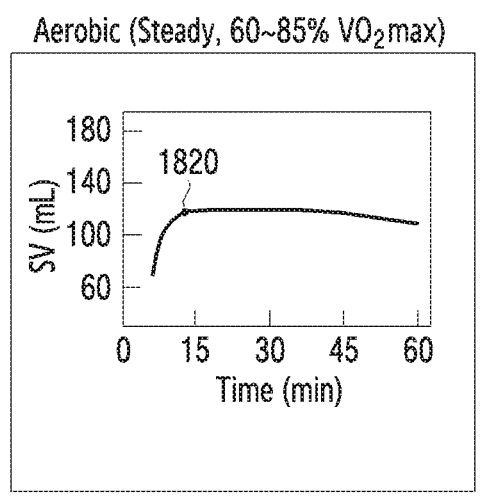
Figure 18C:
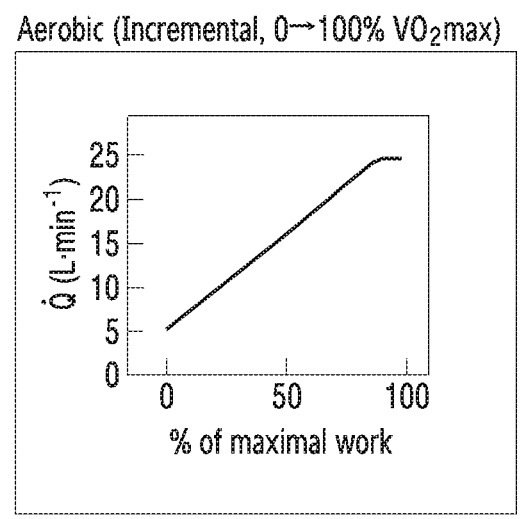
Figure 18D:
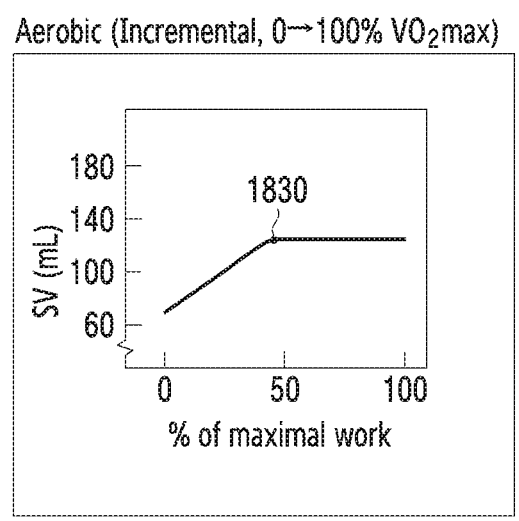

Referring to FIGS. 18A-18D, FIGS. 18A and 18B illustrate second sensor data measured during the first time interval under a steady exercise load, and FIGS. 18C and 18D illustrate second sensor data measured during the first time interval under an incremental increasing load. For example, FIGS. 18A and 18C show cardiac output, and FIGS. 18B and 18D show blood pressure.

As described in FIG. 12, if the first exercise being performed by the user is required to be stopped, the electronic device may output a warning (or notification) to advise the user to stop the currently performed exercise.

The electronic device may output a warning or notification to advise the user to stop the currently performed exercise in the case where variation in the second sensor data shows a specified pattern, as well as in the case where the intensity of the first exercise determined on the basis of the second sensor data satisfies a specified condition.

The electronic device may use at least one of the plurality of pieces of second sensor data shown in FIGS. 18A-18D as an indicator as to whether or not to make a request for stopping the first exercise being performed by the user. For example, if at least one of a plurality of pieces of second sensor data shows a specified pattern, the electronic device may make a request for stopping the first exercise being performed by the user.

The electronic device may make a request for stopping the first exercise being performed by the user on the basis of feature points 1820 and 1830 of SV data, among the blood pressure data shown in FIGS. 18B and 18D. The electronic device may determine information on the maximum blood pressure of the user, or the maximum exercise intensity that the user is able to perform, on the basis of the feature points 1820 and 1830 of the SV data. The electronic device may make a request for stopping the first exercise being performed by the user on the basis of the information on the maximum blood pressure. For example, if the ratio of the current blood pressure of the user to the maximum blood pressure falls within a specified range, the electronic device may make a request for stopping the first exercise being performed by the user.

Figure 19:
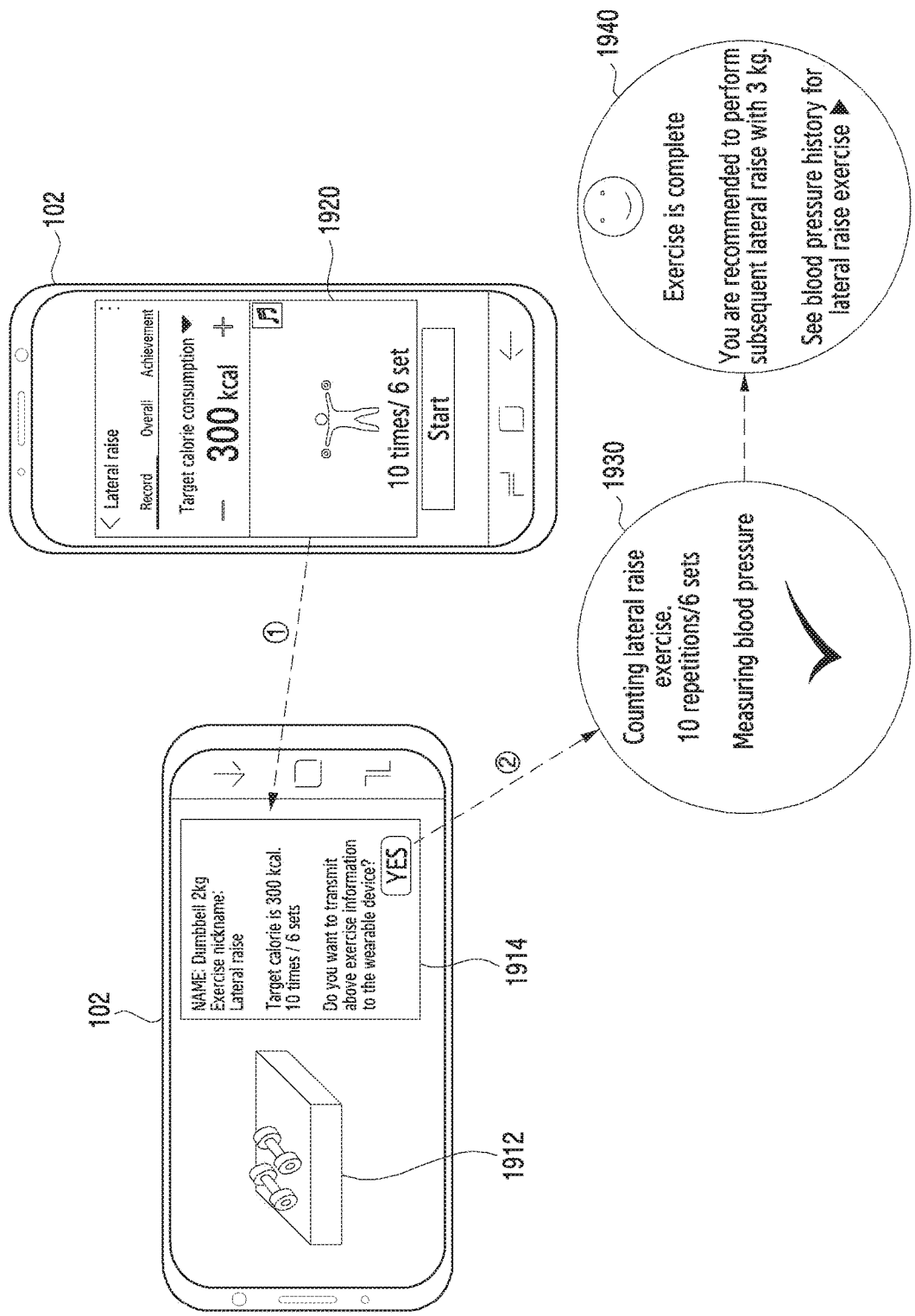
FIG. 19 illustrates an embodiment of obtaining information related to a first exercise through augmented reality (AR) before detecting the start of exercise and providing guidance information to a user according to an embodiment of the disclosure.

FIG. 19 illustrates an embodiment of obtaining information related to the first exercise through augmented reality (AR) before detecting the start of exercise and providing guidance information to the user according to an embodiment of the disclosure.

Referring to FIG. 19, the electronic device 102 may provide guidance information of the exercise, which is to be performed subsequently by the user, on the basis of a user input for executing a specific application (e.g., a healthcare application or a fitness application) installed in the electronic device. The electronic device 102 may provide guidance information of the exercise, which is to be performed subsequently by the user, by executing a specific application or using a specific executed application on the basis of the reception of a user voice input including information about the type of exercise (e.g., squats) and weight (e.g., 100 kg).

The electronic device 102 may provide the guidance information of the exercise, which is to be performed subsequently by the user, on the basis of an operation of detecting that the user performs a specific exercise while a specific application is being executed (e.g., 10 squats, 100 kg). For example, the electronic device 102 may provide guidance information 1920 that recommends that the user perform six sets of 10 lateral raises.

The electronic device 102 may identify whether or not an image is obtained through a camera module on the basis of a user input within a predetermined period of time after providing the guidance information. If it is confirmed that an image has been obtained, the electronic device 102 may identify whether or not the obtained image contains a specific subject 1912 (e.g., dumbbells, barbells, kettlebells, or the like). The electronic device 102 may identify the weight of the lateral raise on the basis of the specific subject. For example, the electronic device 102 may detect text or numbers engraved on the specific subject using an optical character recognition (OCR) method or the like, and may obtain the weight of the lateral raise (e.g., 2 kg) on the basis of the detected text or numbers.

If the guidance information provided from the electronic device includes weight, and if the weight included in the guidance information is different from the weight identified on the basis of the specific subject of the image, the electronic device may determine the weight identified on the basis of the specific subject of the image as the weight of the exercise that was actually performed by the user.

If the obtained image contains a specific subject, the electronic device may display information 1914 related to the specific subject on the obtained image so as to overlap the obtained image. The electronic device may display information 1914 related to the specific subject on the image taken by the user so as to overlap the same through an AR method. The information 1914 related to the specific subject may include guidance information of the subsequent exercise to be performed by the user.

The electronic device may transmit the information 1914 related to the specific subject to another electronic device. The other electronic device may be a wearable device (e.g., the electronic device 103) that measures sensor data of the user (e.g., the first sensor data or the second sensor data). The electronic device may transmit the information 1914 related to the specific subject to another electronic device on the basis of a user input for transmitting the information 1914 related to the specific subject to another electronic device.

The other electronic device may obtain the first sensor data and the second sensor data using a first sensor and a second sensor. The other electronic device may output a notification 1930, which indicates that first sensor data and second sensor data are to be obtained (measured), in various manners.

The other electronic device may detect that the user has completed the exercise on the basis of the first sensor data and the second sensor data, and may further provide guidance information of the exercise to be performed subsequently on the basis of the first sensor data and the second sensor data. For example, the other electronic devices may output a notification in various manners recommending the user to perform the subsequent lateral raise with a weight of 3 kg. For example, the other electronic device may display a notification 1940, which recommends the user to perform the subsequent lateral raise with a weight of 3 kg, may output a sound therefor, or may transmit the same to the electronic device 102.

Figure 21A:
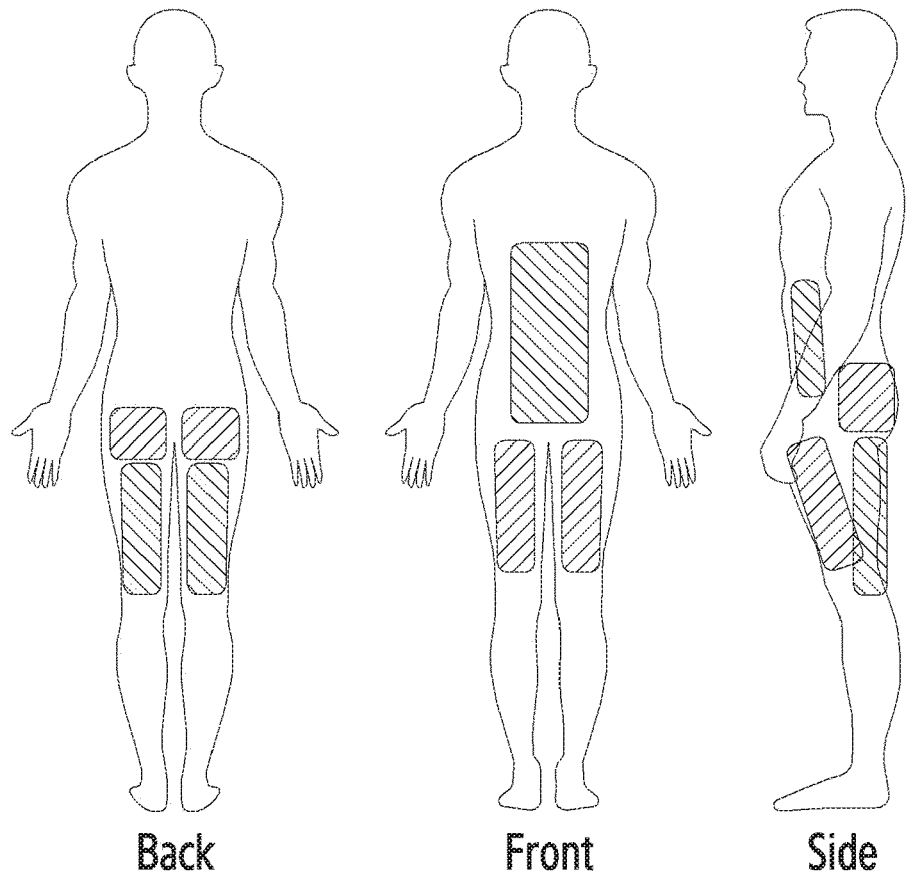
FIGS. 21A and 21B illustrate a body map representing muscles used in performing static exercise according to various embodiments of the disclosure.
Figure 21B:
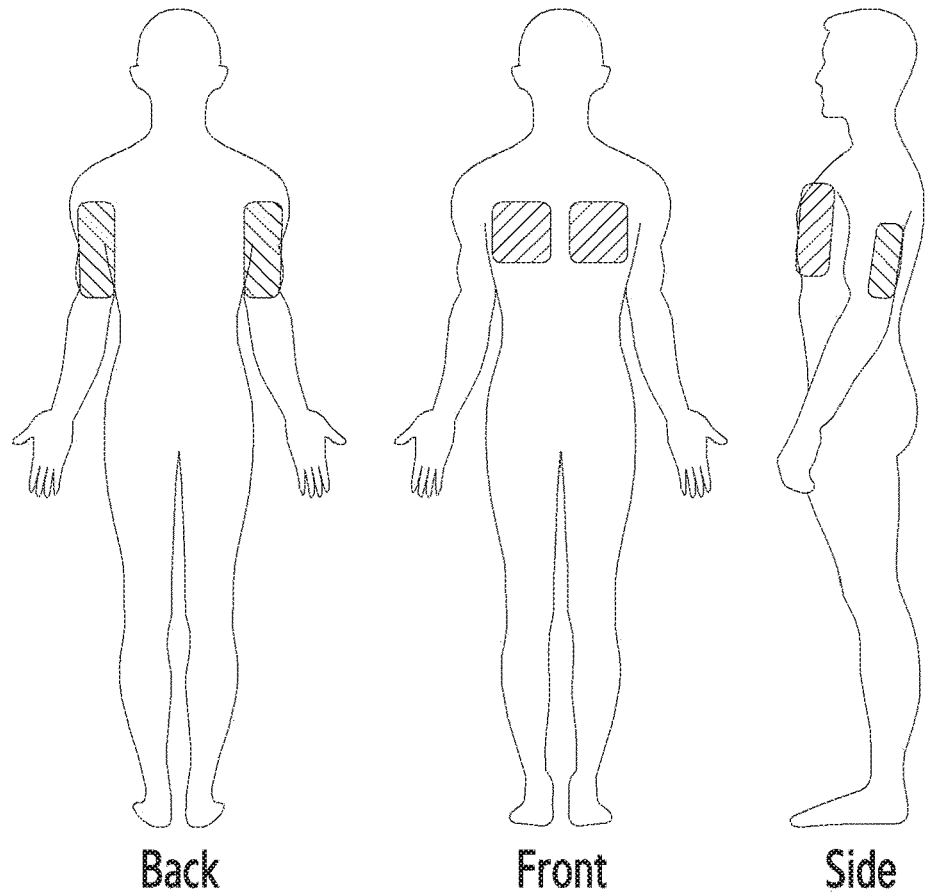

FIGS. 21A and 21B illustrate a body map representing muscles used in performing static exercise according to various embodiments of the disclosure.

Referring to FIGS. 21A and 21B, FIG. 21A shows a body map showing muscles used when performing squat, and FIG. 21B shows a body map showing muscles used when performing flat bench press.

If the user performs static exercise, the body parts to be stimulated are different from each other depending on the type of exercise. In addition, a plurality of body parts may be simultaneously stimulated according to the type of exercise, and the plurality of body parts to be stimulated may be given different degrees of importance depending on the degree of involvement in the actions performed by the user.

For example, referring to FIG. 21A, if the user performs a squat, the quadriceps (front muscles of the thigh) and the gluteus muscles (hip muscles) may be primarily used, and the popliteal muscles (back muscles of the thigh) and abdominal muscles may be secondarily used.

Referring to FIG. 21B, if the user performs a bench press, the pectoralis major muscles (chest muscles) may be primarily used, and the triceps (upper and back muscles of the arm) may be secondarily used.

As described above, since the static exercise uses different muscles depending on the type thereof, in order to maximize the exercise effect through the static exercise, it is necessary to perform various kinds of exercise in various manners (e.g., modification of the number of times and weight such as a pyramid scheme). The various embodiments of the disclosure may be utilized to provide analysis information of the first exercise performed by the user and to provide guidance information of the second exercise to be performed by the user on the basis of interaction with the user in order to maximize the exercise effect through static exercise (and aerobic exercise).

An electronic device according to various embodiments may include a housing; a touch screen display to be exposed through a first portion of the housing; a motion sensor disposed inside the housing; a PPG sensor disposed in a second portion of the housing; a processor operatively coupled to the display, the motion sensor, and the PPG sensor; and a memory operably coupled to the processor, wherein the memory stores instructions that allow the processor, when executed, to: receive first data from the motion sensor; identify whether or not a user has started exercise on the basis of at least some of the first data; receive second data from the PPG sensor after identifying whether or not the user has started exercise; and determine the type of exercise of the user on the basis of at least some of the first data and the second data.

The electronic device may be a wearable device.

The motion sensor may include an acceleration sensor, a gyro sensor, or a proximity sensor.

The instructions may allow the processor to detect the blood pressure of the user on the basis of at least some of the second data.

The instructions may allow the processor to determine whether the type of exercise is static exercise or aerobic exercise on the basis of at least some of the first data and the second data.

The second data may include third data, and the instructions may allow the processor to determine whether the type of exercise is static exercise or aerobic exercise on the basis of at least one of a correlation between the third data or a correlation between the first data and the second data.

The instructions may allow the processor to determine the intensity of the exercise or whether or not to continue to perform the exercise on the basis of at least some of the first data and the second data.

The instructions may allow the processor to display indications on the display on the basis of, at least in part, the intensity of the exercise.

The indications may include text or an image relating to the exercise intensity of the user or whether or not to continue to perform the exercise.

The instructions may allow the processor to determine, after the exercise is performed, the intensity of the exercise or whether or not to continue to perform the exercise on the basis of at least one of a maximum value, a minimum value, a difference between the maximum value and the minimum value, an average slope, and geometric feature points of the second data during the time interval in which the exercise is being performed.

The instructions may allow the processor to display an indication that makes a request for stopping the exercise, while the exercise is being performed, on the basis of at least one of a maximum value, a minimum value, a difference between the maximum value and the minimum value, an average slope, and geometric feature points of the second data from the time point at which the exercise was started to the present time.

The instructions may allow the processor to provide a user interface for receiving user feedback on the exercise after displaying the indication on the display.

The instructions may allow the processor to change at least one threshold value that was used to determine the intensity of the exercise on the basis of user feedback received through the user interface, and store information about the at least one changed threshold value in the memory.

The instructions may allow the processor to provide guidance information of an exercise, which is to be performed subsequent to the exercise by the user, on the basis of at least one piece of user feedback information received through the user interface and the second data.

The guidance information of the exercise, which is to be performed subsequent to the exercise by the user, may include information on the intensity of the exercise to be performed by the user, and the instructions may allow the processor to determine the intensity of the exercise to be performed by the user by assigning weights to the user feedback information and the second data, respectively.

A method of operating an electronic device may include receiving first data from a motion sensor of the electronic device; identifying whether or not a user has started an exercise on the basis of at least some of the first data; receiving second data from a PPG sensor of the electronic device after identifying whether or not a user has started the exercise; and determining the type of exercise performed by the user on the basis of at least some of the first data and the second data.

The method may further include determining the intensity of the exercise or whether or not to continue to perform the exercise on the basis of at least some of the first data and the second data.

The determining the intensity of the exercise or whether or not to continue to perform the exercise may include determining, after the exercise is performed, the intensity of the exercise or whether or not to continue to perform the exercise on the basis of at least one of a maximum value, a minimum value, a difference between the maximum value and the minimum value, an average slope, and geometric feature points of the second data during the time interval in which the exercise is performed.

The method may further include, after providing the user with information about the intensity of the exercise or whether or not to continue to perform the exercise, providing guidance information of an exercise, which is to be performed subsequent to the exercise by the user, on the basis of at least one piece of user feedback information received through a user interface and the second data.

The computer-readable storage medium may include a hard disk, a floppy disk, a magnetic medium (e.g., a magnetic tape), an optical media (e.g., compact disc read-only memory (CD-ROM), digital optical disc (DVD)), a magneto-optical media (e.g., a floptical disk), an inner memory, etc. The instruction may include a code made by a complier or a code that can be executed by an interpreter. The programming module according to the disclosure may include one or more of the aforementioned components or may further include other additional components, or some of the aforementioned components may be omitted. Operations performed by a module, a programming module, or other elements according to various embodiments may be executed sequentially, in parallel, repeatedly, or in a heuristic manner. At least some operations may be executed according to another sequence, may be omitted, or may further include other operations.

An electronic device according to various embodiments of the disclosure may provide a user with information about the type of exercise performed by the user and the intensity thereof on the basis of information of the user, which is measured in real time during the exercise of the user. In addition, an electronic device according to various embodiments may provide recommended exercise information conforming to user's needs and circumstances on the basis of user feedback data. Accordingly, an electronic device according to various embodiments of the disclosure may provide exercise information to meet the user's needs eventually, thereby guiding the user to have an optimal exercise effect.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. An electronic device comprising:
   a housing;
   a display exposed through a first portion of the housing;
   a motion sensor disposed inside the housing;
   a photoplethysmography (PPG) sensor disposed in a second portion of the housing;
   a processor operatively coupled to the display, the motion sensor, and the PPG sensor; and
   a memory operably coupled to the processor,
   wherein the memory stores instructions that, when executed, cause the processor to:
     receive first data from the motion sensor,
     identify whether a user has started exercise based on at least a portion of the first data,
     receive second data from the PPG sensor,
   determine at least one of heart rate data or blood pressure data based on the second data,
     determine a type of the exercise based on at least a portion of the first data and the second data, wherein the type of the exercise includes a first type of the exercise and a second type of the exercise,
     assign weights given to the heart rate and the blood pressure data based on the type of the exercise,
     wherein when the determined type of the exercise is the first type of the exercise, weight of the heart rate data is higher than weight of the blood pressure data, and
     wherein when the determined type of the exercise is the second type of the exercise, the weight of the heart rate data is lower than the weight of the blood pressure data,
     determine an intensity of the exercise based on the assigned weights given to the heart rate and the blood pressure data, and
     control the display to display guidance information of an exercise determined based on the intensity of the exercise.

2. The electronic device of claim 1, wherein the electronic device is a wearable device.

3. The electronic device of claim 1, wherein the motion sensor comprises at least one of an acceleration sensor, a gyro sensor, or a proximity sensor.

4. The electronic device of claim 1, wherein the first type of the exercise is an aerobic exercise, wherein the second type of the exercise is a static exercise.

5. The electronic device of claim 4,
   wherein the second data comprise third data different from the rest of the second data, and
   wherein the instructions further cause the processor to determine whether the type of exercise is static exercise or aerobic exercise based on at least one of a correlation between portions of the third data or a correlation between the first data and the second data.

6. The electronic device of claim 1, wherein the instructions further cause the processor to determine whether to continue to perform the exercise based on the portion of the first data and the second data.

7. The electronic device of claim 6, wherein the instructions further cause the processor to display indications on the display based on, at least in part, the intensity of the exercise.

8. The electronic device of claim 7, wherein the indications comprise text or an image relating to exercise intensity of the user or whether to continue to perform the exercise.

9. The electronic device of claim 6, wherein the instructions further cause the processor to determine, after the exercise has started, the intensity of the exercise or whether to continue to perform the exercise based on at least one of a maximum value, a minimum value, a difference between the maximum value and the minimum value, an average slope, or geometric feature points of the second data during a time interval in which the exercise is performed.

10. The electronic device of claim 7, wherein the instructions further cause the processor to control the display to display an indication that makes a request for stopping of the exercise, while the exercise is being performed, on the basis of at least one of a maximum value, a minimum value, a difference between the maximum value and the minimum value, an average slope, or geometric feature points of the second data from a time point at which the exercise was started to a present time.

11. The electronic device of claim 7, wherein the instructions further cause the processor to provide a user interface for receiving user feedback on the exercise after displaying the indication on the display.

12. The electronic device of claim 11, wherein the instructions further cause the processor to:
   change at least one threshold value that was used to determine the intensity of the exercise based on user feedback received through the user interface, and
   store information about the at least one changed threshold value in the memory.

13. The electronic device of claim 11, wherein the instructions further cause the processor to provide the guidance information of an exercise, which is to be performed subsequent to the exercise by the user, on a basis of at least one piece of user feedback information received through the user interface and the second data.

14. The electronic device of claim 13,
   wherein the guidance information of the exercise, which is to be performed subsequent to the exercise by the user, comprises information on the intensity of the exercise to be performed by the user, and
   wherein the instructions cause the processor to determine the intensity of the exercise to be performed by the user by assigning weights to the user feedback information and the second data, respectively.

15. A method of operating an electronic device, the method comprising:
   receiving first data from a motion sensor of the electronic device;
   identifying whether a user has started an exercise based on at least a portion of the first data;
   receiving second data from a photoplethysmography (PPG) sensor of the electronic device;

determining at least one of heart rate data or blood pressure data based on the second data;

determining a type of exercise of the user based on at least a portion of the first data and the second data, wherein the type of the exercise includes a first type of the exercise and a second type of the exercise;

assigning weights given to the heart rate and the blood pressure data based on the type of the exercise, wherein when the determined type of the exercise is the first type of the exercise, a weight of the heart rate data is higher than a weight of the blood pressure data, and wherein when the determined type of the exercise is the second type of the exercise, the weight of the heart rate data is lower than the weight of the blood pressure data;

determining an intensity of the exercise based on the assigned weights given to the heart rate and the blood pressure data; and displaying guidance information of an exercise determined based on the intensity of the exercise.

16. The method of claim 15, wherein the first type of the exercise is an aerobic exercise, wherein the second type of the exercise is a static exercise, wherein the second data comprises third data different from the rest of the second data, and wherein the determining of the type of exercise comprises determining whether the type of exercise is static exercise or aerobic exercise based on at least one of a correlation between portions of the third data or a correlation between the first data and the second data.

17. The method of claim 15, further comprising determining whether to continue to perform the exercise based on the portion of the first data and the second data.

18. The method of claim 17, wherein the determining of the intensity of the exercise or whether to continue to perform the exercise comprises determining, after the exercise has started, the intensity of the exercise or whether to continue to perform the exercise based on at least one of a maximum value, a minimum value, a difference between the maximum value and the minimum value, an average slope, or geometric feature points of the second data during a time interval in which the exercise is performed.

19. The method of claim 18, further comprising, after providing the user with information about the intensity of the exercise or whether to continue to perform the exercise, providing guidance information of an exercise, which is to be performed subsequent to the exercise by the user, based on user feedback information received through a user interface and the second data.

* * * * *